(12) United States Patent
Rabiner et al.

(10) Patent No.: US 8,684,965 B2
(45) Date of Patent: Apr. 1, 2014

(54) PHOTODYNAMIC BONE STABILIZATION AND DRUG DELIVERY SYSTEMS

(75) Inventors: Robert A. Rabiner, Tiverton, RI (US); Richard Scott Rader, Wayland, MA (US)

(73) Assignee: IlluminOss Medical, Inc., East Providence, RI (US)

( * ) Notice: Subject to any disclaimer, the term of this patent is extended or adjusted under 35 U.S.C. 154(b) by 98 days.

(21) Appl. No.: 13/088,916

(22) Filed: Apr. 18, 2011

(65) Prior Publication Data

US 2011/0313356 A1    Dec. 22, 2011

Related U.S. Application Data

(60) Provisional application No. 61/357,034, filed on Jun. 21, 2010.

(51) Int. Cl.
*A61M 25/10* (2013.01)
*A61M 29/00* (2006.01)

(52) U.S. Cl.
CPC .......... *A61M 25/10* (2013.01); *A61M 25/1011* (2013.01); *A61M 2025/1013* (2013.01); *A61M 2025/105* (2013.01)
USPC ................. 604/101.02; 604/103.02; 606/15

(58) Field of Classification Search
USPC ........... 604/96.01, 101.02, 103.02, 912, 917, 604/919; 606/15, 92–93; 623/17.12, 17.16
See application file for complete search history.

(56) References Cited

U.S. PATENT DOCUMENTS 3,173,418 A * 3/1965 Baran ...................... 128/207.15
4,280,233 A    7/1981 Raab
4,294,251 A   10/1981 Greenwald et al.
4,313,434 A    2/1982 Segal
4,341,691 A    7/1982 Anuta
(Continued)

FOREIGN PATENT DOCUMENTS

DE        40 28 466        3/1992
EP        0 709 698        5/1996
(Continued)

OTHER PUBLICATIONS

PCT International Search Report based on PCT/US11/38389 dated Sep. 22, 2011.

(Continued)

*Primary Examiner* — Quynh-Nhu H Vu
(74) *Attorney, Agent, or Firm* — Greenberg Traurig, LLP; David J. Dykeman; Roman Fayerberg

(57) ABSTRACT

Photodynamic bone stabilization and drug delivery systems are disclosed herein. In an embodiment, a photodynamic bone stabilization and drug delivery system of the present disclosure includes an insertion catheter having an inner void for passing at least one light-sensitive liquid, and an inner lumen; an expandable portion releasably engaging a distal end of the insertion catheter, wherein the expandable portion comprises an inner expandable portion in communication with the inner lumen of the insertion catheter and sufficiently designed to maintain a light-sensitive liquid therein; and an outer expandable portion, surrounding the inner expandable portion, sufficiently designed to house and release at least one additive from the outer expandable portion in an outward direction from the inner expandable portion; and a light-conducting fiber sized to pass through the inner lumen of the insertion catheter and into the inner expandable portion for delivering light energy to the light-sensitive liquid.

20 Claims, 15 Drawing Sheets

(56) References Cited

U.S. PATENT DOCUMENTS

| | | | |
|---|---|---|---|
| 4,369,772 A | 1/1983 | Miller | |
| 4,414,608 A | 11/1983 | Furihata | |
| 4,422,719 A | 12/1983 | Orcutt | |
| 4,433,898 A | 2/1984 | Nasiri | |
| 4,462,394 A | 7/1984 | Jacobs | |
| 4,466,435 A | 8/1984 | Murray | |
| 4,562,598 A | 1/1986 | Kranz | |
| 4,686,973 A | 8/1987 | Frisch | |
| 4,697,584 A | 10/1987 | Haynes | |
| 4,735,625 A | 4/1988 | Davidson | |
| 4,870,953 A | 10/1989 | DonMichael et al. | |
| 4,888,024 A | 12/1989 | Powlan | |
| 4,904,391 A | 2/1990 | Freeman | |
| 4,961,424 A | 10/1990 | Kubota et al. | |
| 4,963,151 A | 10/1990 | Ducheyne et al. | |
| 4,969,888 A * | 11/1990 | Scholten et al. | 606/94 |
| 5,030,093 A | 7/1991 | Mitnick | |
| 5,049,157 A | 9/1991 | Mittelmeier et al. | |
| 5,085,660 A | 2/1992 | Lin | |
| 5,092,899 A | 3/1992 | Forte | |
| 5,102,413 A | 4/1992 | Poddar | |
| 5,108,404 A | 4/1992 | Scholten et al. | |
| 5,112,333 A | 5/1992 | Fixel | |
| 5,295,733 A | 3/1994 | LeBegue | |
| 5,295,962 A * | 3/1994 | Crocker et al. | 604/101.02 |
| 5,303,718 A | 4/1994 | Krajicek | |
| 5,316,550 A | 5/1994 | Forte | |
| 5,336,699 A | 8/1994 | Cooke et al. | |
| 5,354,293 A * | 10/1994 | Beyer et al. | 606/15 |
| 5,372,598 A | 12/1994 | Luhr et al. | |
| 5,391,144 A | 2/1995 | Sakurai et al. | |
| 5,415,654 A | 5/1995 | Daikuzono | |
| 5,423,850 A | 6/1995 | Berger | |
| 5,432,876 A | 7/1995 | Appeldorn et al. | |
| 5,443,468 A | 8/1995 | Johnson | |
| 5,462,552 A | 10/1995 | Kiester | |
| 5,480,400 A | 1/1996 | Berger | |
| 5,538,514 A | 7/1996 | Hawkins | |
| 5,548,676 A | 8/1996 | Savage, Jr. | |
| 5,554,111 A | 9/1996 | Morrey et al. | |
| 5,556,429 A | 9/1996 | Felt | |
| 5,571,204 A | 11/1996 | Nies | |
| 5,658,310 A | 8/1997 | Berger | |
| 5,658,963 A | 8/1997 | Qian et al. | |
| 5,705,181 A | 1/1998 | Cooper et al. | |
| 5,707,374 A | 1/1998 | Schmidt | |
| 5,713,901 A | 2/1998 | Tock | |
| 5,795,353 A | 8/1998 | Felt | |
| 5,824,087 A | 10/1998 | Aspden et al. | |
| 5,827,289 A | 10/1998 | Reiley et al. | |
| 5,888,220 A | 3/1999 | Felt et al. | |
| 5,897,557 A | 4/1999 | Chin et al. | |
| 5,908,433 A | 6/1999 | Eager et al. | |
| 5,972,015 A | 10/1999 | Scribner et al. | |
| 5,980,075 A | 11/1999 | Sheaffer | |
| 5,980,253 A | 11/1999 | Oxman et al. | |
| 5,987,199 A | 11/1999 | Zarian et al. | |
| 5,989,230 A | 11/1999 | Frassica | |
| 6,008,264 A | 12/1999 | Ostler et al. | |
| 6,019,761 A | 2/2000 | Gustilo | |
| 6,019,774 A | 2/2000 | Weiss et al. | |
| 6,033,411 A | 3/2000 | Preissman | |
| 6,039,762 A | 3/2000 | McKay | |
| 6,042,380 A | 3/2000 | De Rowe | |
| 6,048,332 A * | 4/2000 | Duffy et al. | 604/103.08 |
| 6,048,346 A | 4/2000 | Reiley et al. | |
| 6,059,789 A | 5/2000 | Dinger et al. | |
| 6,066,154 A | 5/2000 | Reiley et al. | |
| 6,079,868 A | 6/2000 | Rydell | |
| 6,103,203 A | 8/2000 | Fischer | |
| 6,110,176 A | 8/2000 | Shapira | |
| 6,121,341 A | 9/2000 | Sawhney et al. | |
| 6,127,597 A | 10/2000 | Beyar et al. | |
| 6,140,452 A | 10/2000 | Felt et al. | |
| 6,159,236 A | 12/2000 | Biel | |
| 6,179,852 B1 | 1/2001 | Strickland et al. | |
| 6,195,477 B1 | 2/2001 | Denuto et al. | |
| 6,200,134 B1 | 3/2001 | Kovac et al. | |
| 6,217,581 B1 | 4/2001 | Tolson | |
| 6,223,085 B1 | 4/2001 | Dann et al. | |
| 6,224,630 B1 | 5/2001 | Bao et al. | |
| 6,235,043 B1 | 5/2001 | Reiley et al. | |
| 6,241,734 B1 | 6/2001 | Scribner et al. | |
| 6,248,110 B1 | 6/2001 | Reiley et al. | |
| 6,248,131 B1 | 6/2001 | Felt et al. | |
| 6,258,089 B1 | 7/2001 | Campbell et al. | |
| 6,261,289 B1 | 7/2001 | Levy | |
| 6,280,456 B1 | 8/2001 | Scribner et al. | |
| 6,282,013 B1 | 8/2001 | Ostler et al. | |
| 6,290,382 B1 | 9/2001 | Bourn et al. | |
| 6,299,597 B1 | 10/2001 | Buscemi et al. | |
| 6,306,177 B1 | 10/2001 | Felt et al. | |
| 6,319,255 B1 | 11/2001 | Grundei et al. | |
| 6,332,894 B1 | 12/2001 | Stalcup et al. | |
| 6,336,914 B1 | 1/2002 | Gillespie, III | |
| 6,336,930 B1 | 1/2002 | Stalcup et al. | |
| 6,358,252 B1 | 3/2002 | Shapira | |
| 6,387,098 B1 | 5/2002 | Cole et al. | |
| 6,395,007 B1 | 5/2002 | Bhatnagar et al. | |
| 6,416,531 B2 | 7/2002 | Chen | |
| 6,416,737 B1 | 7/2002 | Manolagas et al. | |
| 6,419,483 B1 | 7/2002 | Adam et al. | |
| 6,423,083 B2 | 7/2002 | Reiley et al. | |
| 6,425,923 B1 | 7/2002 | Stalcup et al. | |
| 6,440,444 B2 | 8/2002 | Boyce et al. | |
| 6,443,988 B2 | 9/2002 | Felt et al. | |
| 6,447,514 B1 | 9/2002 | Stalcup et al. | |
| 6,458,375 B1 | 10/2002 | Gertzman et al. | |
| 6,478,751 B1 | 11/2002 | Krueger et al. | |
| 6,485,512 B1 | 11/2002 | Cheng | |
| 6,494,883 B1 | 12/2002 | Ferree | |
| 6,524,251 B2 | 2/2003 | Rabiner et al. | |
| 6,524,313 B1 | 2/2003 | Fassier et al. | |
| 6,551,321 B1 | 4/2003 | Burkinshaw et al. | |
| 6,551,337 B1 | 4/2003 | Rabiner et al. | |
| 6,565,528 B1 | 5/2003 | Mueller | |
| 6,579,277 B1 | 6/2003 | Rabiner et al. | |
| 6,579,279 B1 | 6/2003 | Rabiner et al. | |
| 6,620,185 B1 | 9/2003 | Harvie et al. | |
| 6,623,505 B2 | 9/2003 | Scribner et al. | |
| 6,632,235 B2 | 10/2003 | Weikel et al. | |
| 6,648,881 B2 | 11/2003 | KenKnight et al. | |
| 6,652,547 B2 | 11/2003 | Rabiner et al. | |
| 6,652,587 B2 | 11/2003 | Felt et al. | |
| 6,660,013 B2 | 12/2003 | Rabiner et al. | |
| 6,679,873 B2 | 1/2004 | Rabiner et al. | |
| 6,695,781 B2 | 2/2004 | Rabiner et al. | |
| 6,695,782 B2 | 2/2004 | Rabiner et al. | |
| 6,696,073 B2 | 2/2004 | Boyce et al. | |
| 6,716,216 B1 | 4/2004 | Boucher et al. | |
| 6,719,773 B1 | 4/2004 | Boucher et al. | |
| 6,726,691 B2 | 4/2004 | Osorio et al. | |
| 6,730,048 B1 | 5/2004 | Hare et al. | |
| 6,733,451 B2 | 5/2004 | Rabiner et al. | |
| 6,733,513 B2 | 5/2004 | Boyle et al. | |
| 6,740,093 B2 | 5/2004 | Hochschuler et al. | |
| 6,755,862 B2 | 6/2004 | Keynan | |
| 6,783,530 B1 | 8/2004 | Levy | |
| 6,802,835 B2 | 10/2004 | Rabiner et al. | |
| 6,818,018 B1 | 11/2004 | Sawhney | |
| 6,852,095 B1 | 2/2005 | Ray | |
| 6,866,678 B2 | 3/2005 | Shenderova et al. | |
| 6,869,442 B2 | 3/2005 | Cheng | |
| 6,875,212 B2 | 4/2005 | Shaolian et al. | |
| 6,885,246 B2 | 4/2005 | Tsutsui et al. | |
| 6,887,246 B2 | 5/2005 | Bhatnagar et al. | |
| 6,887,275 B2 | 5/2005 | Carchidi et al. | |
| 6,899,713 B2 | 5/2005 | Shaolian et al. | |
| 6,899,719 B2 | 5/2005 | Reiley et al. | |
| 6,932,843 B2 | 8/2005 | Smith et al. | |
| 6,964,667 B2 | 11/2005 | Shaolian et al. | |
| 6,979,341 B2 | 12/2005 | Scribner et al. | |
| 6,981,981 B2 | 1/2006 | Reiley et al. | |
| 7,001,431 B2 | 2/2006 | Bao et al. | |

(56) References Cited

U.S. PATENT DOCUMENTS

| | | |
|---|---|---|
| 7,008,433 B2 | 3/2006 | Voellmicke et al. |
| 7,052,498 B2 | 5/2006 | Levy et al. |
| 7,077,865 B2 | 7/2006 | Bao et al. |
| 7,124,067 B2 | 10/2006 | Ascenzi |
| 7,141,061 B2 | 11/2006 | Williams et al. |
| 7,144,414 B2 | 12/2006 | Harvie et al. |
| 7,153,305 B2 | 12/2006 | Johnson et al. |
| 7,156,861 B2 | 1/2007 | Scribner et al. |
| 7,156,880 B2 | 1/2007 | Evans et al. |
| 7,169,140 B1 | 1/2007 | Kume |
| 7,215,863 B1 | 5/2007 | Arenella et al. |
| 7,241,303 B2 | 7/2007 | Reiss et al. |
| 7,258,692 B2 | 8/2007 | Thelen et al. |
| 7,261,720 B2 | 8/2007 | Stevens et al. |
| 7,320,709 B2 | 1/2008 | Felt et al. |
| 7,341,601 B2 | 3/2008 | Eisermann et al. |
| 7,360,542 B2 | 4/2008 | Nelson et al. |
| 7,407,616 B2 | 8/2008 | Melikechi et al. |
| 7,419,450 B2 | 9/2008 | Ito |
| 7,427,295 B2 | 9/2008 | Ellman et al. |
| 7,547,319 B2 | 6/2009 | Segal et al. |
| 7,628,800 B2 * | 12/2009 | Sherman et al. ............... 606/279 |
| 7,632,277 B2 | 12/2009 | Woll et al. |
| 7,632,291 B2 | 12/2009 | Stephens et al. |
| 7,666,205 B2 | 2/2010 | Weikel et al. |
| 7,722,620 B2 | 5/2010 | Truckai et al. |
| 7,744,555 B2 | 6/2010 | DiMauro et al. |
| 7,766,965 B2 | 8/2010 | Bao et al. |
| 7,771,476 B2 | 8/2010 | Justis et al. |
| 7,776,075 B2 | 8/2010 | Bruneau et al. |
| 7,806,900 B2 | 10/2010 | Rabiner |
| 7,811,284 B2 | 10/2010 | Rabiner |
| 7,811,286 B2 | 10/2010 | Medoff |
| 7,811,290 B2 | 10/2010 | Rabiner |
| 7,842,040 B2 | 11/2010 | Rabiner et al. |
| 7,850,711 B1 | 12/2010 | Stone et al. |
| 7,879,041 B2 | 2/2011 | Rabiner et al. |
| 7,912,539 B2 | 3/2011 | Doty et al. |
| 7,947,015 B2 | 5/2011 | Herweck et al. |
| 8,034,071 B2 | 10/2011 | Scribner et al. |
| 8,123,807 B2 | 2/2012 | Kim et al. |
| 8,210,729 B2 | 7/2012 | O'Leary et al. |
| 8,246,628 B2 | 8/2012 | Rabiner |
| 8,328,402 B2 | 12/2012 | O'Leary et al. |
| 8,348,956 B2 | 1/2013 | Rabiner |
| 8,366,711 B2 | 2/2013 | Rabiner et al. |
| 8,403,968 B2 | 3/2013 | Rabiner et al. |
| 8,413,664 B2 | 4/2013 | Appling |
| 8,512,338 B2 | 8/2013 | Rabiner et al. |
| 2001/0011174 A1 | 8/2001 | Reiley et al. |
| 2001/0044626 A1 | 11/2001 | Reiley et al. |
| 2002/0156482 A1 | 10/2002 | Scribner et al. |
| 2002/0161373 A1 | 10/2002 | Osorio et al. |
| 2002/0198526 A1 | 12/2002 | Shaolian et al. |
| 2003/0028210 A1 | 2/2003 | Boyle et al. |
| 2003/0083642 A1 | 5/2003 | Boyd et al. |
| 2003/0105469 A1 | 6/2003 | Karmon |
| 2003/0114914 A1 | 6/2003 | Cheng |
| 2003/0156431 A1 | 8/2003 | Gozum et al. |
| 2003/0199850 A1 | 10/2003 | Chavez et al. |
| 2003/0212426 A1 | 11/2003 | Olson et al. |
| 2003/0229372 A1 | 12/2003 | Reiley et al. |
| 2004/0006341 A1 | 1/2004 | Shaolian et al. |
| 2004/0024388 A1 | 2/2004 | Altshuler |
| 2004/0034434 A1 | 2/2004 | Evans et al. |
| 2004/0059333 A1 | 3/2004 | Carl et al. |
| 2004/0059417 A1 | 3/2004 | Smith et al. |
| 2004/0092948 A1 | 5/2004 | Stevens et al. |
| 2004/0098015 A1 | 5/2004 | Weikel et al. |
| 2004/0117025 A1 | 6/2004 | Reindel |
| 2004/0133280 A1 | 7/2004 | Trieu |
| 2004/0167561 A1 | 8/2004 | Boucher et al. |
| 2004/0167625 A1 | 8/2004 | Beyar et al. |
| 2004/0225296 A1 | 11/2004 | Reiss et al. |
| 2004/0228142 A1 | 11/2004 | Takada et al. |
| 2004/0230309 A1 | 11/2004 | Di Mauro et al. |
| 2004/0247641 A1 | 12/2004 | Felt et al. |
| 2004/0260239 A1 * | 12/2004 | Kusleika ................. 604/101.02 |
| 2005/0010231 A1 | 1/2005 | Myers |
| 2005/0015140 A1 | 1/2005 | deBeer |
| 2005/0015148 A1 | 1/2005 | Jansen et al. |
| 2005/0043733 A1 | 2/2005 | Eisermann et al. |
| 2005/0043808 A1 | 2/2005 | Felt et al. |
| 2005/0049691 A1 | 3/2005 | Mericle et al. |
| 2005/0090901 A1 * | 4/2005 | Studer ........................ 623/17.12 |
| 2005/0119662 A1 | 6/2005 | Reiley et al. |
| 2005/0142315 A1 | 6/2005 | DeSimone et al. |
| 2005/0149022 A1 | 7/2005 | Shaolian et al. |
| 2005/0159749 A1 | 7/2005 | Levy et al. |
| 2005/0171604 A1 | 8/2005 | Michalow |
| 2005/0192671 A1 | 9/2005 | Bao et al. |
| 2005/0197711 A1 | 9/2005 | Cachia |
| 2005/0228260 A1 | 10/2005 | Burwell et al. |
| 2005/0234453 A1 | 10/2005 | Shaolian et al. |
| 2005/0251140 A1 | 11/2005 | Shaolian et al. |
| 2005/0284485 A9 | 12/2005 | Nelson et al. |
| 2006/0009550 A1 | 1/2006 | Messersmith et al. |
| 2006/0015105 A1 | 1/2006 | Warren et al. |
| 2006/0036253 A1 | 2/2006 | Leroux et al. |
| 2006/0084985 A1 | 4/2006 | Kim et al. |
| 2006/0100547 A1 | 5/2006 | Rabiner et al. |
| 2006/0100635 A1 | 5/2006 | Reiley et al. |
| 2006/0100706 A1 | 5/2006 | Shadduck et al. |
| 2006/0111726 A1 | 5/2006 | Felt et al. |
| 2006/0122625 A1 | 6/2006 | Truckai et al. |
| 2006/0142747 A1 | 6/2006 | Appling |
| 2006/0155296 A1 | 7/2006 | Richter |
| 2006/0173464 A1 | 8/2006 | Ellman et al. |
| 2006/0183811 A1 | 8/2006 | Melikechi et al. |
| 2006/0184246 A1 | 8/2006 | Zwirkoski |
| 2006/0190022 A1 * | 8/2006 | Beyar et al. ................... 606/192 |
| 2006/0195165 A1 | 8/2006 | Gertner et al. |
| 2006/0217747 A1 | 9/2006 | Ferree |
| 2006/0229617 A1 | 10/2006 | Meller et al. |
| 2006/0247787 A1 | 11/2006 | Rydell et al. |
| 2006/0253102 A1 | 11/2006 | Nance et al. |
| 2006/0253200 A1 | 11/2006 | Bao et al. |
| 2006/0258981 A1 | 11/2006 | Eidenschink |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2006/0265077 A1 | 11/2006 | Zwirkoski |
| 2006/0271061 A1 | 11/2006 | Beyar et al. |
| 2006/0276793 A1 | 12/2006 | Berry |
| 2006/0276819 A1 | 12/2006 | Osorio et al. |
| 2006/0282169 A1 | 12/2006 | Felt et al. |
| 2006/0287730 A1 | 12/2006 | Segal et al. |
| 2007/0027547 A1 | 2/2007 | Rydell et al. |
| 2007/0067032 A1 | 3/2007 | Felt et al. |
| 2007/0087031 A1 | 4/2007 | Ashman et al. |
| 2007/0118143 A1 | 5/2007 | Ralph et al. |
| 2007/0123876 A1 | 5/2007 | Czartoski et al. |
| 2007/0123877 A1 | 5/2007 | Goldin et al. |
| 2007/0123878 A1 | 5/2007 | Shaver et al. |
| 2007/0150061 A1 * | 6/2007 | Trieu ........................ 623/17.12 |
| 2007/0161991 A1 | 7/2007 | Altarac et al. |
| 2007/0198023 A1 | 8/2007 | Sand et al. |
| 2007/0225705 A1 | 9/2007 | Osario et al. |
| 2007/0255287 A1 | 11/2007 | Rabiner |
| 2008/0015500 A1 | 1/2008 | Herweck et al. |
| 2008/0021474 A1 | 1/2008 | Bonutti et al. |
| 2008/0039715 A1 * | 2/2008 | Wilson et al. ................. 600/424 |
| 2008/0039854 A1 | 2/2008 | Rabiner |
| 2008/0080205 A1 | 4/2008 | Forrester et al. |
| 2008/0103505 A1 | 5/2008 | Fransen |
| 2008/0125784 A1 | 5/2008 | Rabiner et al. |
| 2008/0154368 A1 | 6/2008 | Justis |
| 2008/0154373 A1 | 6/2008 | Protopsaltis et al. |
| 2008/0183122 A1 | 7/2008 | Fisher et al. |
| 2008/0188858 A1 | 8/2008 | Luzzi et al. |
| 2008/0234820 A1 | 9/2008 | Felt et al. |
| 2008/0249529 A1 | 10/2008 | Zarda et al. |
| 2008/0255560 A1 | 10/2008 | Myers et al. |
| 2008/0269750 A1 | 10/2008 | Justin |

(56) References Cited

U.S. PATENT DOCUMENTS

| | | | |
|---|---|---|---|
| 2008/0287951 A1 | 11/2008 | Stoneburner et al. | |
| 2009/0018524 A1 | 1/2009 | Greenhalgh et al. | |
| 2009/0024166 A1 | 1/2009 | Carl et al. | |
| 2009/0048629 A1 | 2/2009 | Rabiner | |
| 2009/0054900 A1* | 2/2009 | Rabiner et al. | 606/93 |
| 2009/0093887 A1 | 4/2009 | Walter et al. | |
| 2009/0112196 A1 | 4/2009 | Rabiner et al. | |
| 2009/0171265 A1* | 7/2009 | Doty et al. | 604/21 |
| 2009/0171358 A1 | 7/2009 | Chang et al. | |
| 2009/0177204 A1 | 7/2009 | Colleran et al. | |
| 2009/0182336 A1 | 7/2009 | Brenzel et al. | |
| 2009/0187192 A1 | 7/2009 | Rabiner et al. | |
| 2009/0216232 A1 | 8/2009 | Buford, III et al. | |
| 2009/0228007 A1 | 9/2009 | Justin et al. | |
| 2009/0254064 A1* | 10/2009 | Boatman | 604/509 |
| 2009/0287309 A1 | 11/2009 | Walch et al. | |
| 2010/0010307 A1* | 1/2010 | Schramm | 600/120 |
| 2010/0234958 A1 | 9/2010 | Linares | |
| 2010/0241178 A1* | 9/2010 | Tilson et al. | 606/86 R |
| 2010/0249942 A1 | 9/2010 | Goswami et al. | |
| 2010/0256641 A1 | 10/2010 | Rabiner et al. | |
| 2010/0262069 A1 | 10/2010 | Rabiner et al. | |
| 2010/0262188 A1 | 10/2010 | Rabiner et al. | |
| 2010/0265733 A1* | 10/2010 | O'Leary et al. | 362/555 |
| 2010/0318087 A1 | 12/2010 | Scribner et al. | |
| 2010/0331850 A1 | 12/2010 | Rabiner | |
| 2011/0004213 A1 | 1/2011 | Rabiner et al. | |
| 2011/0009871 A1 | 1/2011 | Rabiner | |
| 2011/0029093 A1 | 2/2011 | Bojarski et al. | |
| 2011/0046746 A1 | 2/2011 | Rabiner et al. | |
| 2011/0098713 A1 | 4/2011 | Rabiner et al. | |
| 2011/0110114 A1 | 5/2011 | Papac et al. | |
| 2011/0118740 A1 | 5/2011 | Rabiner et al. | |
| 2011/0160870 A1 | 6/2011 | Baumgartner et al. | |
| 2011/0166306 A1 | 7/2011 | Stansbury et al. | |
| 2012/0165941 A1 | 6/2012 | Rabiner et al. | |
| 2012/0262939 A1 | 10/2012 | O'Leary et al. | |
| 2012/0289968 A1 | 11/2012 | Rabiner | |
| 2013/0003406 A1 | 1/2013 | O'Leary et al. | |
| 2013/0006304 A1 | 1/2013 | Rabiner et al. | |
| 2013/0013008 A1 | 1/2013 | Rabiner et al. | |
| 2013/0013009 A1 | 1/2013 | Colleran et al. | |
| 2013/0013010 A1 | 1/2013 | Rabiner et al. | |
| 2013/0023876 A1 | 1/2013 | Rabiner et al. | |
| 2013/0023877 A1 | 1/2013 | Rabiner et al. | |
| 2013/0023886 A1 | 1/2013 | Rabiner et al. | |
| 2013/0041472 A1 | 2/2013 | Rabiner et al. | |
| 2013/0046390 A1 | 2/2013 | Rabiner et al. | |
| 2013/0066326 A1 | 3/2013 | Rabiner et al. | |
| 2013/0158607 A1 | 6/2013 | Rabiner et al. | |
| 2013/0184715 A1 | 7/2013 | Rabiner et al. | |

FOREIGN PATENT DOCUMENTS

| | | |
|---|---|---|
| JP | 2001-527437 | 12/2001 |
| JP | 2004-526525 | 9/2002 |
| JP | 2005-511143 | 4/2005 |
| JP | 2006-212425 | 8/2006 |
| NL | 9001858 | 3/1992 |
| WO | WO 98/38918 | 9/1998 |
| WO | WO 02/43628 | 6/2002 |
| WO | WO 03/047472 | 6/2003 |
| WO | WO 2004/045393 | 6/2004 |
| WO | WO 2004/058045 | 7/2004 |
| WO | WO 2004/073563 | 9/2004 |
| WO | WO 2004/112661 | 12/2004 |
| WO | WO 2005/112804 | 12/2005 |
| WO | WO 2006/016807 | 2/2006 |
| WO | WO 2007/059259 | 5/2007 |
| WO | WO 2007/127255 | 11/2007 |
| WO | WO 2007/127260 | 11/2007 |
| WO | WO 2008/039811 | 4/2008 |
| WO | WO 2008/063265 | 5/2008 |
| WO | WO 2009/059090 | 5/2009 |
| WO | WO 2009/082688 | 7/2009 |
| WO | WO 2009/131999 | 10/2009 |
| WO | WO 2010/050965 | 5/2010 |
| WO | WO 2010/118158 | 10/2010 |
| WO | WO 2011/060062 | 5/2011 |
| WO | WO 2011/071567 | 6/2011 |
| WO | WO 2011/162910 | 12/2011 |
| WO | WO 2012/088432 | 6/2012 |
| WO | WO 2013/013069 | 1/2013 |
| WO | WO 2013/013071 | 1/2013 |
| WO | WO 2013/013072 | 1/2013 |
| WO | WO2013/059609 | 4/2013 |

OTHER PUBLICATIONS

USPTO Office Action in U.S. Appl. No. 11/964,370 mailed Sep. 23, 2011.
USPTO Office Action in U.S. Appl. No. 12/858,924 mailed Oct. 24, 2011.
PCT International Search Report based on PCT/US11/66871 dated May 1, 2012.
USPTO Office Action in U.S. Appl. No. 12/875,460 mailed Mar. 8, 2012.
USPTO Office Action in U.S. Appl. No. 11/964,370 mailed Mar. 16, 2012.
USPTO Office Action in U.S. Appl. No. 12/858,924 mailed Apr. 4, 2012.
USPTO Office Action in U.S. Appl. No. 12/756,014 mailed May 11, 2012.
Jovanovic et al., "Fixion Nails for Humeral Fractures, Injury", Int. J. Care Injured, vol. 35, Issue 11, pp. 1140-1142, Nov. 2004.
Maruyama et al., "Metacarpal Fracture Fixation with Absorbable Polyglycolide Rods and Stainless Steel K Wires: A Biomechanical Comparison", Journal of Biomedical Materials Research (Applied Biomaterials), vol. 33, Issue 1, pp. 9-12, Apr. 1996.
Waris et al., "Bioabsorbable Miniplating Versus Metallic Fixation for Metacarpal Fractures", Clinical Orthopaedics and Related Research, No. 410, pp. 310-319, May 2003.
Waris et al., "Self-Reinforced Bioabsorbable Versus Metallic Fixation Systems for Metacarpal and Phalangeal Fractures: A Biomechanical Study", The Journal of Hand Surgery, vol. 27A, No. 5, pp. 902-909, Sep. 2002.
International Search Report based on PCT/US07/20402 dated Apr. 1, 2008.
International Search Report based on PCT/US07/10050 dated Apr. 17, 2008.
International Search Report based on PCT/US07/10038 dated Aug. 27, 2008.
International Search Report based on PCT/US08/81929 dated Jan. 12, 2009.
International Search Report based on PCT/US08/81924 dated Feb. 9, 2009.
International Search Report based on PCT/US08/87630 dated Feb. 24, 2009.
International Search Report based on PCT/US10/30275 dated Aug. 11, 2010.
International Search Report based on PCT/US10/56219 dated Jan. 20, 2011.
International Search Report based on PCT/US10/46003 dated May 24, 2011.
Office Action in U.S. Appl. No. 11/789,906 mailed Apr. 29, 2009.
Office Action in U.S. Appl. No. 11/789,906 mailed Mar. 11, 2010.
Office Action in U.S. Appl. No. 11/789,906 mailed Apr. 30, 2010.
Office Action in U.S. Appl. No. 11/789,907 mailed May 11, 2010.
Office Action in U.S. Appl. No. 11/903,123 mailed Jul. 1, 2010.
Office Action in U.S. Appl. No. 12/262,411 mailed Sep. 1, 2010.
Office Action in U.S. Appl. No. 11/964,370 mailed Dec. 9, 2010.
Office Action in U.S. Appl. No. 11/964,370 mailed Apr. 28, 2011.
USPTO Office Action in U.S. Appl. No. 12/262,370 mailed May 29, 2012.
USPTO Office Action in U.S. Appl. No. 12/943,544 mailed Jun. 8, 2012.
USPTO Office Action in U.S. Appl. No. 12/886,288 mailed Jun. 26, 2012.

(56) References Cited

OTHER PUBLICATIONS

USPTO Office Action in U.S. Appl. No. 11/964,370 mailed Jul. 6, 2012.
Extended European Search Report based on EP 07 75 6022 dated Jul. 30, 2012.
Extended European Search Report based on EP 07 75 6016 dated Jul. 30, 2012.
USPTO Office Action in U.S. Appl. No. 12/755,784 mailed Aug. 1, 2012.
USPTO Office Action in U.S. Appl. No. 12/858,924 mailed Aug. 2, 2012.
USPTO Office Action in U.S. Appl. No. 12/886,288 mailed Aug. 15, 2012.
PCT International Search Report based on PCT/US12/47447 dated Oct. 2, 2012.
PCT International Search Report based on PCT/US12/47446 dated Oct. 15, 2012.
PCT International Search Report based on PCT/US12/47444 dated Oct. 18, 2012.
USPTO Office Action in U.S. Appl. No. 12/756,014 mailed Oct. 25, 2012.
USPTO Office Action in U.S. Appl. No. 12/755,784 mailed Dec. 23, 2011.
USPTO Office Action in U.S. Appl. No. 12/886,288 mailed Dec. 27, 2011.
USPTO Office Action in U.S. Appl. No. 12/859,680 mailed Nov. 9, 2012.
USPTO Office Action in U.S. Appl. No. 12/943,544 mailed Dec. 3, 2012.
USPTO Office Action in U.S. Appl. No. 12/859,680 mailed Jan. 17, 2013.
USPTO Office Action in U.S. Appl. No. 12/262,370 mailed Dec. 14, 2012.
International Search Report and Written Opinion for PCT/US2012/061047 mailed Jan. 7, 2013.
USPTO Office Action in U.S. Appl. No. 12/756,014 mailed Jan. 22, 2013.
Supplemental European Search Report based on EP 08 87 7881 dated May 15, 2013.
USPTO Office Action in U.S. Appl. No. 13/617,557 mailed Feb. 4, 2013.
USPTO Office Action in U.S. Appl. No. 12/755,784 mailed Mar. 13, 2013.
USPTO Office Action in U.S. Appl. No. 13/616,416 mailed Mar. 25, 2013.
USPTO Office Action in U.S. Appl. No. 13/561,249 mailed Apr. 23, 2013.
USPTO Office Action in U.S. Appl. No. 12/262,370 mailed Apr. 26, 2013.
USPTO Office Action in U.S. Appl. No. 13/772,947 mailed Jun. 19, 2013.
USPTO Office Action in U.S. Appl. No. 12/859,680 mailed Jul. 9, 2013.
USPTO Office Action in U.S. Appl. No. 13/561,249 mailed Sep. 16, 2013.
USPTO Office Action in U.S. Appl. No. 12/943,544 mailed Sep. 25, 2013.
USPTO Office Action in U.S. Appl. No. 13/617,557 mailed Oct. 9, 2013.

* cited by examiner

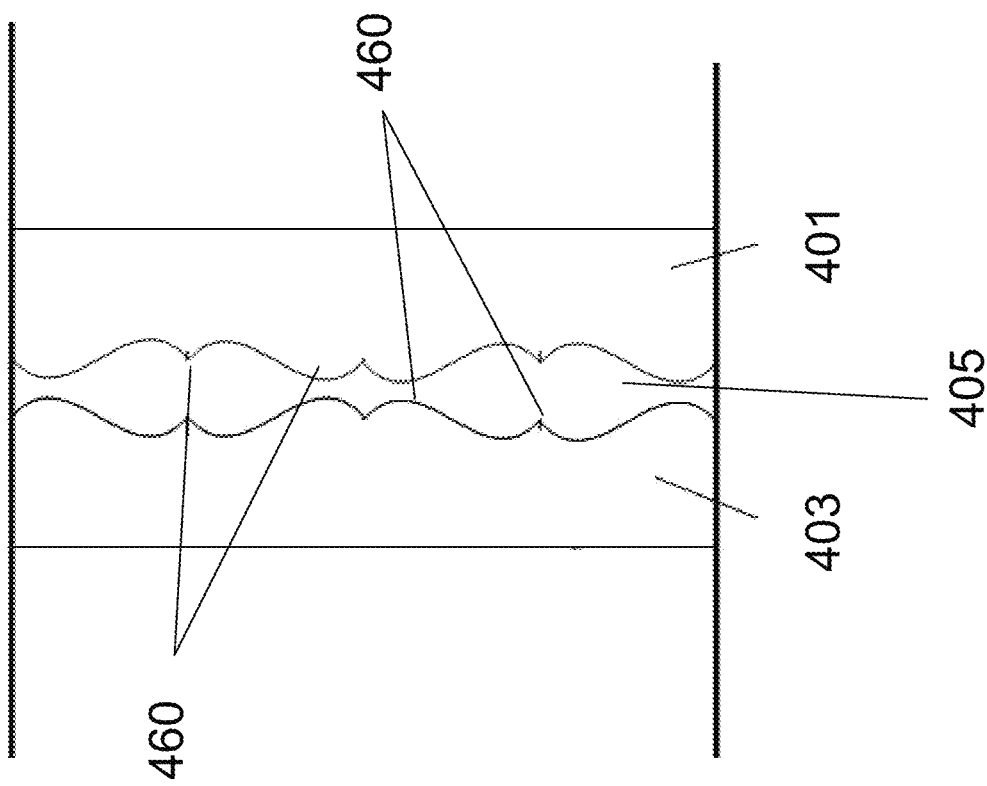

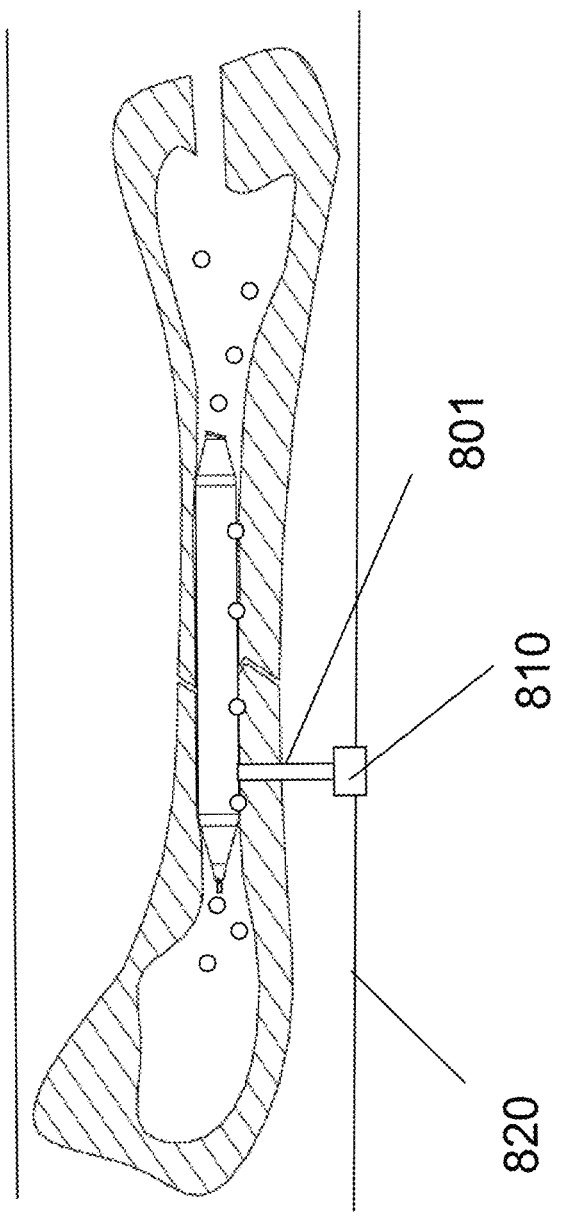

PHOTODYNAMIC BONE STABILIZATION AND DRUG DELIVERY SYSTEMS

RELATED APPLICATIONS

This application claims the benefit of and priority to U.S. Provisional Patent Application No. 61/357,034, filed on Jun. 21, 2010, the entirety of this application is hereby incorporated herein by reference for the teachings therein.

FIELD

The embodiments disclosed herein relate to minimally invasive orthopedic procedures, and more particularly to photodynamic bone stabilization and drug delivery systems for fracture fixation.

BACKGROUND

The basic goal of fracture fixation is to stabilize the fractured bone, to enable fast healing of the injured bone, and to return early mobility and full function of the injured extremity. Fractures can be treated conservatively or with external and internal fixation. Complications associated with internal fixation include, but are not limited to, inadequate immobilization of the fractured bone which may develop into a non-union, and the development of deep wound infections, which may cause significant morbidity.

SUMMARY

Photodynamic bone stabilization and drug delivery systems are disclosed herein. According to aspects illustrated herein, there is provided a photodynamic bone stabilization and drug delivery system that includes an insertion catheter having an elongated shaft with a proximal end, a distal end, and a longitudinal axis therebetween, the insertion catheter having an inner void for passing at least one light-sensitive liquid, and an inner lumen; an expandable portion releasably engaging the distal end of the insertion catheter, wherein the expandable portion comprises: an inner expandable portion fabricated from a non-permeable material, wherein the inner expandable portion is in communication with the inner lumen of the insertion catheter and wherein the inner expandable portion is sufficiently designed to maintain a light-sensitive liquid within the inner expandable portion; and an outer expandable portion, surrounding the inner expandable portion, sufficiently designed to house and release at least one additive from the outer expandable portion in an outward direction from the inner expandable portion; and a light-conducting fiber, wherein the light-conducting fiber is sized to pass through the inner lumen of the insertion catheter and into the inner expandable portion for delivering light energy to the light-sensitive liquid.

According to aspects illustrated herein, there is provided a photodynamic bone stabilization and drug delivery system that includes an insertion catheter having an elongated shaft with a proximal end, a distal end, and a longitudinal axis therebetween, the insertion catheter having an inner void for passing at least one light-sensitive liquid, and an inner lumen; an expandable portion releasably engaging the distal end of the insertion catheter, wherein the expandable portion is movable from a deflated state to an inflated state when a light-sensitive liquid is delivered to the expandable portion; one or more surface layers disposed along an outer surface of the expandable portion, wherein the one or more surface layers are sufficiently designed to release at least one additive; and a light-conducting fiber, wherein the light-conducting fiber is sized to pass through the inner lumen of the insertion catheter and into the expandable portion for delivering light energy to the light-sensitive liquid.

According to aspects illustrated herein, there is provided a method for repairing a fractured bone that includes the steps of delivering to an inner cavity of the fractured bone an expandable portion releasably engaging a distal end of an insertion catheter, wherein the expandable portion comprises: an inner expandable portion fabricated from a non-permeable material, wherein the inner expandable portion is in communication with an inner lumen of the insertion catheter and wherein the inner expandable portion is sufficiently designed to maintain a light-sensitive liquid within the inner expandable portion; and an outer expandable portion, surrounding the inner expandable portion, sufficiently designed to house and release at least one additive from the outer expandable portion in an outward direction from the inner expandable portion; and infusing a light-sensitive liquid through an inner void of the insertion catheter into the inner expandable portion to move the expandable portion from an initial deflated state to a final inflated state; inserting a light-conducting fiber into the inner lumen of the insertion catheter; activating the light-conducting fiber so as to cure the light sensitive liquid within the inner expandable portion; delivering at least one additive locally to the fractured bone by releasing the at least one additive from the outer expandable portion; and releasing the expandable portion from the insertion catheter.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 4B shows a side view of an embodiment of the expandable portion of FIG. 4A.

FIGS. 8A-8E illustrate an embodiment of a procedure for repairing a weakened or fractured bone. FIG. 8A is a side view of an embodiment of a distal end of a photodynamic bone stabilization and drug delivery system for repairing a weakened or fractured bone positioned within a fractured bone. The distal end of the expandable portion releasably engages a catheter. FIG. 8B is a side view of the expandable portion of FIG. 8A after a light-sensitive liquid monomer has been added to the expandable portion, causing the expandable portion to inflate. FIG. 8C is a side view of the expandable portion of FIG. 8A after a light-conducting fiber has been inserted into the expandable portion to transmit energy to initiate a curing process. FIG. 8D is a side view of the hardened expandable portion of FIG. 8A positioned within the weakened or fractured bone after the catheter has been released. FIG. 8E is a side view of another embodiment of the hardened expandable portion positioned within the weakened or fractured bone after the catheter has been released.

Figure 1:
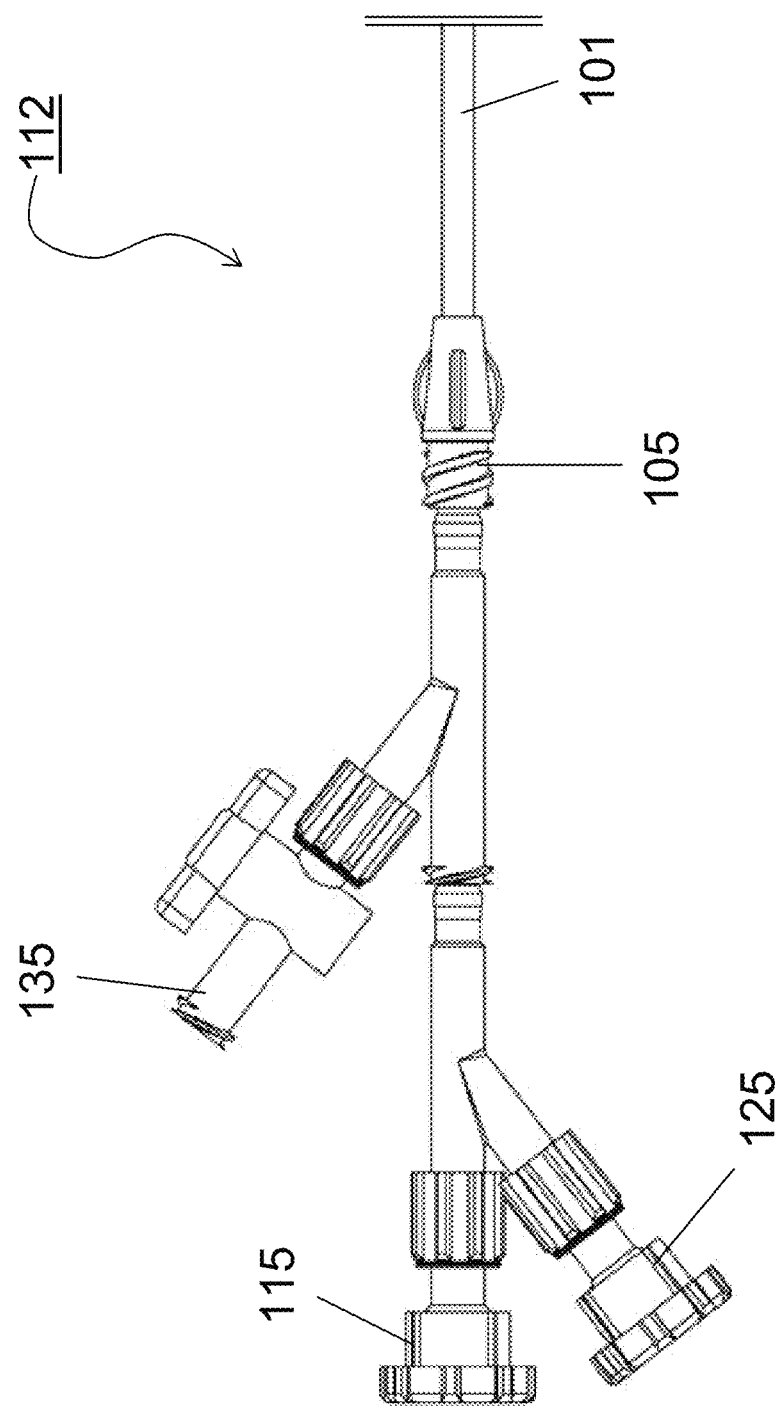
FIG. 1 shows a side view of an embodiment of a proximal end of a photodynamic bone stabilization and drug delivery system for repairing a weakened or fractured bone according to the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The embodiments disclosed herein relate to minimally invasive orthopedic procedures, and more particularly to photodynamic bone stabilization and drug delivery systems. In an embodiment, a photodynamic bone stabilization and drug delivery system of the present disclosure is used in repairing a weakened or fractured bone. In an embodiment, a photodynamic bone stabilization and drug delivery system of the present disclosure is used to deliver at least one additive locally to a weakened or fractured bone. In an embodiment, a photodynamic bone stabilization and drug delivery system of the present disclosure is used to deliver at least one additive locally to a site of repair, while allowing the user to alter the rate of delivery, duration of delivery, concentration of at least one additive and number of additives at any time during the healing process.

In an embodiment, a photodynamic bone stabilization and drug delivery system of the present disclosure is used to deliver drugs from outside of the patient body to a location inside the body, particularly into the intramedullary canal of a bone. In an embodiment, the drugs are site specific deliverables. In an embodiment, the drugs are physician specified. In an embodiment, a photodynamic bone stabilization and drug delivery system of the present disclosure includes an external communication port connected to an external drug delivery device, such as a syringe pump, so that drugs can be delivered to the intramedullary cavity from the external drug delivery device. In an embodiment, the drugs are held in an external reservoir and are delivered to the implanted expandable portion of the photodynamic bone stabilization and drug delivery system by the pump to be released into the intramedullary canal over a period of time. In an embodiment, the concentration or combination of drugs delivered to the intramedullary canal can be changed at any time during the healing process as determined by a physician. In an embodiment, the external communication port to the intramedullary canal can be disconnected when no longer necessary without further disruption or intervention to the intramedullary canal.

In an embodiment, a photodynamic bone stabilization and drug delivery system of the present disclosure allows for the delivery of physician specified drugs and agents from a site external to the intramedullary canal into the intramedullary canal. In an embodiment, a photodynamic bone stabilization and drug delivery system of the present disclosure allows for the sustained delivery of physician specified drugs and agents into the intramedullary canal from an external fluid reservoir using a pump delivery system. In an embodiment, a photodynamic bone stabilization and drug delivery system of the present disclosure is used to deliver physician specified drugs and agents into the intramedullary canal from a site external to the intramedullary canal via a conductive catheter fluidly connected to the system, wherein the conductive catheter can be disconnected from the system without entering the intramedullary canal. In an embodiment, a photodynamic bone stabilization and drug delivery system of the present disclosure enables site specific delivery into the intramedullary canal from external location of physician specified drugs, agents to treat infection, improve bone growth, or chemotherapy agents.

In an embodiment, a photodynamic bone stabilization and drug delivery system of the present disclosure is used to deliver at least one antibiotic locally to a weakened or fractured bone to prevent or treat an infection in the bone. In an embodiment, a photodynamic bone stabilization and drug delivery system of the present disclosure is used to deliver at least one bone growth factor locally to a weakened or fractured bone to induce formation of new bone. In an embodiment, a photodynamic bone stabilization and drug delivery system of the present disclosure is used to deliver at least one bisphosphonate locally to a weakened or fractured bone to prevent the loss of bone mass. In an embodiment, a photodynamic bone stabilization and drug delivery system of the present disclosure is used to deliver at least one chemotherapeutic agent.

In an embodiment, a photodynamic bone stabilization and drug delivery system of the present disclosure is used to treat a fracture including, but not limited to, a hand fracture, a wrist fracture, a radius fracture, an ulna fracture, a clavicle fracture, a metacarpal fracture, a phalanx fracture, a metatarsal fracture, a phalange fracture, a tibia fracture, a fibula fracture, a humerus fracture, and a rib fracture. Long bones are the large bones in the arms and legs, and include the humerus, the radius/ulna, the femur and the tibia/fibula. In an embodiment, a photodynamic bone stabilization and drug delivery system of the present disclosure is used to reinforce a fractured long bone. In an embodiment, a photodynamic bone stabilization and drug delivery system of the present disclosure is used to stabilize a fractured long bone in conjunction with anatomic reduction (i.e., proper reorientation of fractured elements to their original position, both relative to one another and relative to other adjacent anatomical features).

FIG. 1 shows an embodiment of a proximal end 112 of a flexible insertion catheter 101 of a photodynamic bone stabilization and drug delivery system of the present disclosure for repairing a weakened or fractured bone. The photodynamic bone stabilization and drug delivery system includes a thin-walled, non-compliant, expandable portion (not visible in FIG. 1) releasably mounted at a distal end of the flexible insertion catheter 101. The insertion catheter 101 may include one or more inner lumens, such as for passing a light-sensitive liquid or an additive, to the expandable portion.

Figure 2A:
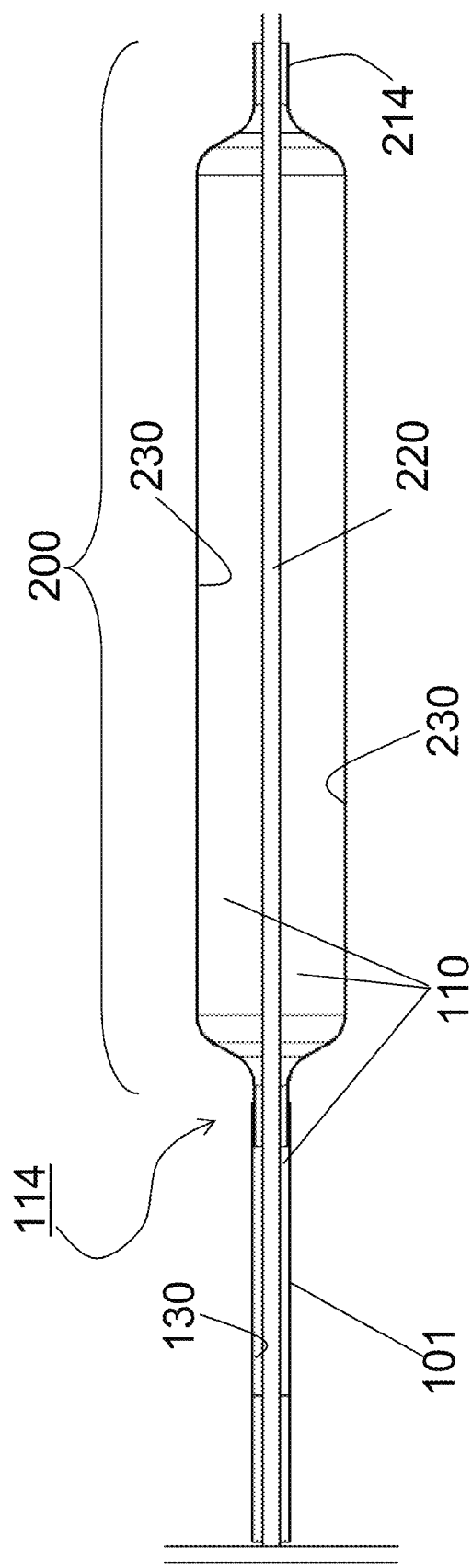
FIGS. 2A-2B show a side view of embodiments of a distal end of a photodynamic bone stabilization and drug delivery system for repairing a weakened or fractured bone according to the present disclosure. The distal end includes an expandable portion (illustrated in an expanded position) sufficiently designed to stabilize the bone, the expandable portion having an internal through hole that extends past a distal surface of the expandable portion for local delivery of at least one additive to the bone.
Figure 2B:
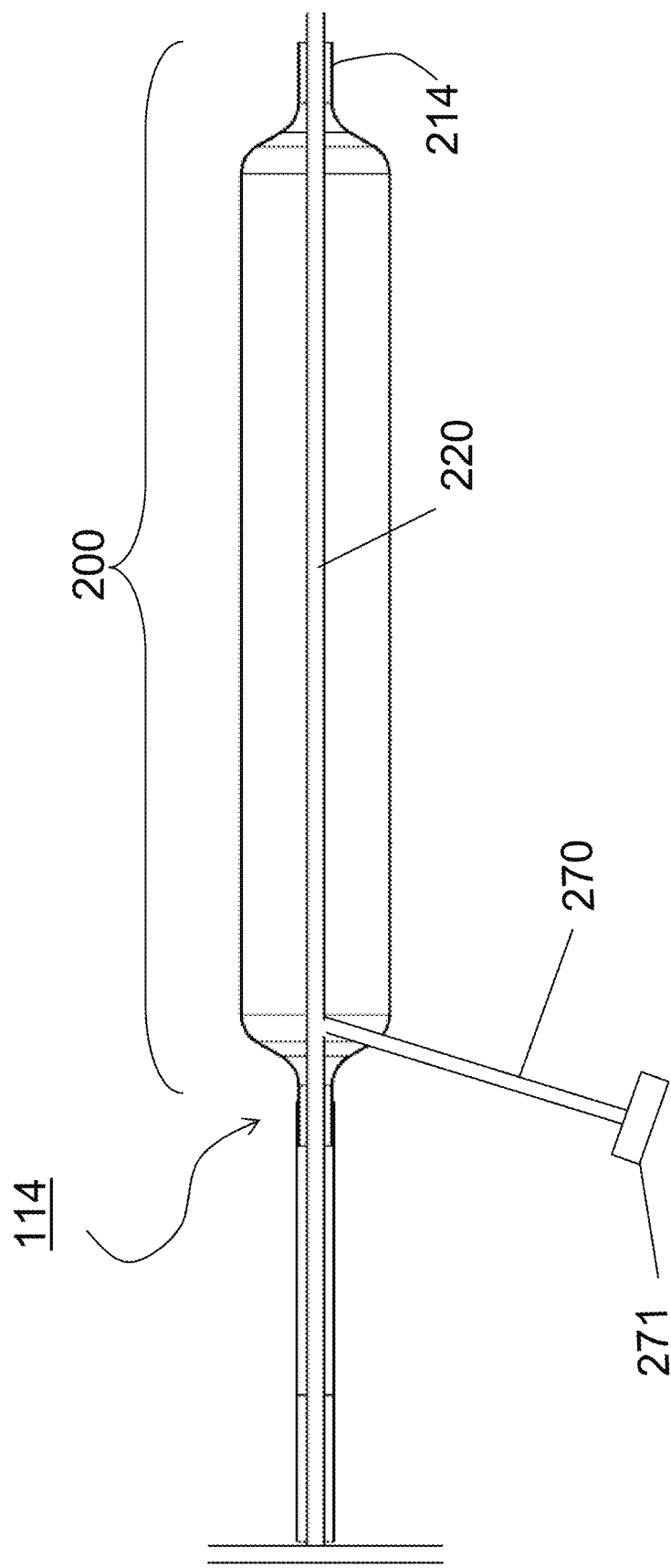

In an embodiment, the expandable portion includes a single thin-walled, non-compliant, expandable portion with an internal through hole that extends past a distal surface of the expandable portion for local delivery of at least one additive to the bone (see FIG. 2A and FIG. 2B). In an embodiment, the expandable portion includes a single thin-walled, non-compliant, expandable portion having an outer surface layer, the outer surface layer being made from electrospun nanofibers and incorporating at least one additive for local delivery of the additive to the bone (see FIG. 3A and FIG. 3B). In an embodiment, the expandable portion includes two thin-walled, non-compliant, expandable portions, wherein an inner expandable portion is sufficiently designed to stabilize the bone, and wherein an outer expandable portion sufficiently designed to release at least one additive housed between the inner expandable portion and the outer expandable portion (see FIG. 4A). In an embodiment, the flexible insertion catheter 101 and/or the expandable portion includes one or more radiopaque markers or bands positioned at various locations. The one or more radiopaque bands, using radiopaque materials such as barium sulfate, tantalum, or other materials known to increase radiopacity, allows a medical professional to view the photodynamic bone stabilization and drug delivery system using fluoroscopy techniques.

A proximal end adapter 105 includes at least one arm and at least one adapter which can be utilized for the infusion and withdrawal of fluids or as conduits for the introduction of devices (e.g., a light-conducting fiber). In an embodiment, an adapter is a Luer lock. In an embodiment, an adapter is a Tuohy-Borst connector. In an embodiment, an adapter is a multi-functional adapter. FIG. 1 shows a side view of a three arm proximal end fitting having three adapters 115, 125, and 135. Adapter 115 can accept, for example, a light-conducting fiber. Adapter 125 can accept, for example, air, cooling fluid, an antibiotic, and a bone growth factor. In an embodiment, adapter 125 can accept, for example, a cooling medium. In an embodiment, adapter 125 can accept, for example, a solution of antibiotic. In an embodiment, adapter 125 can accept, for example, a solution of bone growth additive. In an embodiment, adapter 125 can accept, for example, pressurizing medium. Adapter 135 can accept, for example, a syringe housing a light-sensitive liquid. In an embodiment, the light-sensitive liquid is a liquid monomer comprising an initiator, wherein the initiator is activated when the light-conducting fiber transmits light energy. In an embodiment, the viscosity of the light-sensitive liquid is about 1000 cP or less. In an embodiment, the light-sensitive liquid has a viscosity ranging from about 650 cP to about 450 cP. Low viscosity allows filling of the expandable portion through a very small delivery system.

In an embodiment, a syringe housing light-sensitive liquid is attached to the adapter 135 at the proximal end 112 of the insertion catheter 101, and during use of the photodynamic bone stabilization and drug delivery system, the syringe plunger is pushed, allowing the syringe to expel the light-sensitive liquid into an inner void 110 (not visible in FIG. 1) of the photodynamic bone stabilization and drug delivery system. As the light-sensitive liquid is expelled through the inner void, it reaches the expandable portion to move the expandable portion from a deflated state to an inflated state. The light-sensitive liquid can be aspirated and reinfused as necessary, allowing for adjustments to the expandable portion prior to curing of the light-sensitive liquid, wherein curing of the light-sensitive liquid hardens the expandable portion in a desired position to stabilize the fracture. These properties allow a user to achieve maximum fracture reduction prior to activating a light source and converting the liquid monomer into a hard polymer.

In an embodiment, a syringe housing at least one additive is attached to the adapter 125 at the proximal end 112 of the insertion catheter 101, and during use of the photodynamic bone stabilization and drug delivery system, the syringe plunger is pushed, allowing the syringe to expel the additive into the expandable portion.

In an embodiment, the light-sensitive liquid may be provided as a unit dose. As used herein, the term "unit dose" is intended to mean an effective amount of light sensitive liquid adequate for a single session. By way of a non-limiting example, a unit dose of a light sensitive liquid of the present disclosure for expanding the one or more inner balloons may be defined as enough light-sensitive liquid to expand the one or more inner balloons so that the expanded one ore more inner balloons substantially fill the space created by the outer balloon. The volume of space created by the outer balloon may vary somewhat from user to user. Thus, a user using a unit dose may have excess light-sensitive liquid left over. It is desirable to provide enough light-sensitive liquid that even the above-average user will have an effective amount of realignment. In an embodiment, a unit dose of a light-sensitive liquid of the present disclosure is contained within a container. In an embodiment, a unit dose of a light-sensitive liquid of the present disclosure is contained in an ampoule. In an embodiment, the expandable member is sufficiently shaped to fit within a space or a gap in a fractured bone. In an embodiment, the light-sensitive liquid can be delivered under low pressure via a standard syringe attached to the port. The light-sensitive liquid can be aspirated and re-infused as necessary, allowing for adjustments to the inmost inner balloon or the intermediate inner balloon. These properties allow a user to achieve maximum fracture reduction prior to activating a light source and converting the liquid monomer into a hard polymer.

In an embodiment, a contrast material may be added to the light-sensitive liquid and/or inflation fluid without significantly increasing the viscosity. Contrast materials include, but are not limited to, barium sulfate, tantalum, or other contrast materials known in the art. The light-sensitive liquid can be aspirated and re-infused as necessary, allowing for thickness adjustments to the one or more inner balloons prior to activating the light source and converting the liquid monomer into a hard polymer. Low viscosity allows filling of the one or more inner balloons through a very small delivery system.

In an embodiment, a light-conducting fiber communicating light from a light source is introduced into adapter 115 at the proximal end 112 of the insertion catheter 101 to pass the light-conducting fiber within an inner lumen 120 (not visible in FIG. 1) of the photodynamic bone stabilization and drug delivery system. In an embodiment, the light-conducting fiber is an light-conducting fiber Light-conducting fibers may be used in accordance with the present disclosure to communicate light from the light source to the remote location. Light-conducting fibers use a construction of concentric layers for optical and mechanical advantages. The most basic function of a fiber is to guide light, i.e., to keep light concentrated over longer propagation distances—despite the natural tendency of light beams to diverge, and possibly even under conditions of strong bending. In the simple case of a step-index fiber, this guidance is achieved by creating a region with increased refractive index around the fiber axis, called the fiber core, which is surrounded by the cladding. The cladding may be protected with a polymer coating. Light is kept in the "core" of the light-conducting fiber by total internal reflection. Cladding keeps light traveling down the length of the fiber to a destination. In some instances, it is desirable to conduct electromagnetic waves along a single guide and extract light along a given length of the guide's distal end rather than only at the guide's terminating face.

In some embodiments of the present disclosure, at least a portion of a length of an light-conducting fiber is modified, e.g., by removing the cladding, in order to alter the direction, propagation, amount, intensity, angle of incidence, uniformity and/or distribution of light. In an embodiment, the light-conducting fiber emits light radially in a uniform manner, such as, for example, with uniform intensity, along a length of the light-conducting fiber in addition to or instead of emitting light from its terminal end/tip. To that end, all or part of the cladding along the length of the light-conducting fiber may be removed. It should be noted that the term "removing cladding" includes taking away the cladding entirely to expose the light-conducting fiber as well as reducing the thickness of the cladding. In addition, the term "removing cladding" includes forming an opening, such as a cut, a notch, or a hole, through the cladding. In an embodiment, removing all or part of the cladding may alter the propagation of light along the light-conducting fiber. In another embodiment, removing all or part of the cladding may alter the direction and angle of incidence of light exuded from the light-conducting fiber.

The light-conducting fiber can be made from any material, such as glass, silicon, silica glass, quartz, sapphire, plastic, combinations of materials, or any other material, and may have any diameter, as not all embodiments of the present disclosure are intended to be limited in this respect. In an embodiment, the light-conducting fiber is made from a polymethyl methacrylate core with a transparent polymer cladding. The light-conducting fiber can have a diameter between approximately 0.75 mm and approximately 2.0 mm. In some embodiments, the light-conducting fiber can have a diameter of about 0.75 mm, about 1 mm, about 1.5 mm, about 2 mm, less than about 0.75 mm or greater than about 2 mm as not all embodiments of the present disclosure are intended to be limited in this respect. In an embodiment, the light-conducting fiber is made from a polymethyl methacrylate core with a transparent polymer cladding. It should be appreciated that the above-described characteristics and properties of the light-conducting fibers are exemplary and not all embodiments of the present disclosure are intended to be limited in these respects. Light energy from a visible emitting light source can be transmitted by the light-conducting fiber. In an embodiment, visible light having a wavelength spectrum of between about 380 nm to about 780 nm, between about 400 nm to about 600 nm, between about 420 nm to about 500 nm, between about 430 nm to about 440 nm, is used to cure the light-sensitive liquid.

The light-sensitive liquid remains a liquid monomer until activated by the light-conducting fiber (cures on demand). Radiant energy from the light-conducting fiber is absorbed and converted to chemical energy to quickly polymerize the monomer. This cure affixes the expandable portion in an expanded shape. A cure may refer to any chemical, physical, and/or mechanical transformation that allows a composition to progress from a form (e.g., flowable form) that allows it to be delivered through the inner void in the insertion catheter 101, into a more permanent (e.g., cured) form for final use in vivo. For example, "curable" may refer to uncured composition, having the potential to be cured in vivo (as by catalysis or the application of a suitable energy source), as well as to a composition in the process of curing (e.g., a composition formed at the time of delivery by the concurrent mixing of a plurality of composition components).

The presently disclosed embodiments provide expandable portions of photodynamic bone stabilization and drug delivery systems of the present disclosure. It should be understood that any of the expandable portions disclosed herein may include one or more radiopaque markers or bands. For example, a radiopaque ink bead may be placed at a distal end of the expandable portion for alignment of the system during fluoroscopy. The one or more radiopaque bands and radiopaque ink bead, using radiopaque materials such as barium sulfate, tantalum, or other materials known to increase radiopacity, allows a medical professional to view the expandable portion during positioning to properly position the expandable during a repair procedure, and allows the medical professional to view the expandable portion during inflation and/or deflation to properly stabilize and align the fractured bones. In an embodiment, the one or more radiopaque bands permit visualization of any voids that may be created by air that gets entrapped in the expandable portion. In an embodiment, the one or more radiopaque bands permit visualization to preclude the expandable portion from misengaging or not meeting a bone due to improper inflation to maintain a uniform expandable/bone interface. In an embodiment, an expandable portion can be sputter coated with a metal material to provide radiopacity and/or reflectivity. Other biocompatible materials can be used to both increase radiopacity and reflectivity of the light in the expandable portion to improve or aid in the curing of the light-sensitive liquid.

It should be understood that an expandable portion disclosed herein may be round, flat, cylindrical, oval, rectangular or any desired shape for a given application. An expandable portion may be formed of a pliable, resilient, conformable, and strong material, including but not limited to urethane, polyethylene terephthalate (PET), nylon elastomer and other similar polymers. In an embodiment, an expandable portion is constructed out of a PET nylon aramet or other non-consumable materials. In an embodiment, an expandable portion may be formed from a material that allows the expandable portion to conform to obstructions or curves at the site of implantation.

An expandable portion disclosed herein is sufficiently designed to deliver additives such as antibiotics, antifungal agents, antimicrobial agents, bisphosphonates, chemotherapeutic agents, growth factors and proteins locally to the site of repair. In an embodiment, such additives are termed drugs—chemical substance used in the treatment, cure, prevention, or diagnosis of disease or used to otherwise enhance physical or mental well-being. For example, after a minimally invasive surgical procedure an infection may develop in a patient, requiring the patient to undergo antibiotic treatment. At least one antibiotic drug may be delivered locally from the expandable portion to the inner cavity of the bone to prevent or combat a possible infection (osteomyelitis). Examples of antibiotics include, but are not limited to, erythromycin, ciprofloxacin, augmentin, levofloxacin, clindamycin, cefuroxine, flucloxacillin, vancomycin, Nafcillin, cefazolin, cephalosporin, ceftazidime, ceftriaxone, Cefepime, piperacillin-tazobactam, ticarcillin-clavulanic acid, and ampicillin-sulbactam, metronidazole. At least one growth factor may be delivered locally from the expandable portion to the inner cavity of the bone to induce the formation of new bone (osteogenesis). Examples of chemotherapeutic agents include, but are not limited to, taxane (docetaxel), doxorubicin, mitomycin C, valrubicin, epirubicin, thiotepa, interferon alpha and other cytokines with therapeutic activities. Moreover, chemotherapeutic agents may be selected from anticancer agents, such, as by the way of a non-limiting example, hypochlorous acid, mitoxantrone, camptothecin, cisplatin, bleomycin, cyclophosphamide, methotrexate, streptozotocin, actinomycin D, vincristine, vinblastine, cystine arabinoside, anthracyclines, alkylative agents, platinum compounds, antimetabolites, nucleoside analogs, methotrexate, purine and pyrimidine analogs, adriamycin, daunomycin, mitomycin, epirubicin, 5-FU, and aclacinomycin. Examples of growth factors include, but are not limited to, insulin-like growth factors (IGFs), transforming growth factors-βs (TGFβs) and bone morphogenetic proteins (BMPs). At least one bisphosphonate may be delivered locally from the expandable portion to the inner cavity of the bone to prevent the loss of bone mass. In an embodiment, an additive can mean a single additive or a combination of additives.

Additives can be delivered, for example, in solution form, in powder form, encapsulated in nanoparticles (such as liposomes), encapsulated in microparticles (such as microspheres, microcapsules and beads), as polymer-drug compounds, or incorporated/impregnated into a scaffold of select shape and size. The solution, powder, nanoparticles, microparticles, compounds and scaffolds are sufficiently designed to release the additive from the expandable portion at an appropriate time for a given application. In an embodiment, an additive may be as a unit dose. As used herein, the term "unit dose" of an additive is intended to mean an effective amount of additive adequate to be delivered for a given amount of time. In an embodiment, the viscosity of the additive solution is controlled so that sufficient release of the additive at the site is achieved. In an embodiment, at least one additive may be pressurized to a pressure sufficient to cause the release of the at least one additive at a desired rate. An additive formulation has a drug-loading sufficient to deliver therapeutic levels of the additive. In an embodiment, the at least one additive is part of a porous polymer-drug compound selected from the group consisting of a porous polymer-drug foam, a porous polymer-drug sponge, a porous polymer-drug fabric, a porous polymer-drug sheet, a porous polymer-drug roll, a porous polymer-drug microparticle or a porous polymer-drug non-woven material. In an embodiment, the porous polymer-drug compound is manufactured from a thermoplastic material selected from the group consisting of Ultra-High Molecular Weight Polyethylene (UHMWPE), High-Density Polyethylene (HDPE), Polypropylene (PP), PTFE, PVDF, EVA, Nylon-6, Polyurethane (PE) and PE/PP Co-polymer. The rate of release and availability of the additive may be regulated so that the quantity of an additive which is released at a particular time or at a particular site is relatively constant and uniform over extended periods of time. The release rate of the additive(s) from a formulation can be selected to last a few hours, a few days, or a few weeks. In an embodiment, additives may be re-filled, if desired. In an embodiment, the additive is released from a bioerodible, bioresorbable, non-toxic, biocompatible hydrophilic polymer matrix. The factors influencing the release of additive from hydrophilic matrices include viscosity of the polymer, ratio of the polymer to additive, mixtures of polymers, compression pressure, thickness of the final product, particle size of the additive, pH of the matrix, entrapped air in the final product, molecular size of the additive, molecular geometry of the additive, solubility of the additive, the presence of excipients, and the mode of incorporation of these substances.

In an embodiment, the expandable portion has a diameter between about 4 mm and about 11 mm. In an embodiment, the expandable portion has a length between 30 mm to 220 mm. In an embodiment, the expandable portion has a diameter ranging from about 5 mm to about 20 mm. In an embodiment, the expandable portion has a length ranging from about 20 mm to about 450 mm. In an embodiment, the expandable portion has a diameter of about 4 mm and a length of about 30 mm or about 40 mm. In an embodiment, the expandable portion has a diameter of about 5 mm and a length of about 30 mm, about 40 mm, about 50 mm, about 60 mm, or about 70 mm. In an embodiment, the expandable portion has a diameter of about 6 mm and a length of about 30 mm, about 40 mm, about 50 mm, about 60 mm, about 70 mm or about 80 mm. In an embodiment, the expandable portion has a diameter of about 7 mm and a length of about 30 mm, about 40 mm, about 50 mm, about 60 mm, about 70 mm, about 80 mm, about 120 mm, about 160 mm, about 180 mm, about 200 mm or about 220 mm. In an embodiment, the expandable portion has a diameter of about 8 mm and a length of about 50 mm, about 60 mm, about 70 mm, about 80 mm, about 120 mm, about 160 mm, about 180 mm, about 200 mm or about 220 mm. In an embodiment, the expandable portion has a diameter of about 9 mm and a length of about 120 mm, about 160 mm, about 180 mm, about 200 mm or about 220 mm. In an embodiment, the expandable portion has a diameter of about 11 mm and a length of about 120 mm, about 160 mm, about 180 mm, about 200 mm or about 220 mm. In an embodiment, the expandable portion has a tapered diameter of about 11 mm to 8 mm and a length of about 120 mm, about 160 mm, about 180 mm, about 200 mm or about 220 mm. In an embodiment, the expandable portion has a diameter of about 5 mm and a length of about 30 mm. In an embodiment, the expandable portion has a diameter of about 5 mm and a length of about 40 mm. In an embodiment, the expandable portion has a diameter of about 6 mm and a length of about 30 mm. In an embodiment, the expandable portion has a diameter of about 6 mm and a length of about 40 mm. In an embodiment, the expandable portion has a diameter of about 6 mm and a length of about 50 mm. In an embodiment, the expandable portion has a diameter of about 7 mm and a length of about 30 mm. In an embodiment, the expandable portion has a diameter of about 7 mm and a length of about 40 mm. In an embodiment, the expandable portion has a diameter of about 7 mm and a length of about 50 mm. In an embodiment, the expandable portion has a diameter of about 14 mm and a length of about 400 mm. In an embodiment, the expandable portion has a diameter of about 14 mm and a length of about 300 mm. It should be understood that an expandable portion disclosed herein by way of example, but not of limitation It should be understood that an expandable portion disclosed herein typically does not have any valves. One benefit of having no valves is that the expandable portion may be inflated or deflated as much as necessary to assist in the fracture reduction and placement. Another benefit of the expandable portion having no valves is the efficacy and safety of the system. Since there is no communication passage of light-sensitive liquid to the body there cannot be any leakage of liquid because all the liquid is contained within the expandable portion. In an embodiment, a permanent seal is created between the expandable portion that is both hardened and affixed prior to the insertion catheter being removed. The expandable portion may have valves, as all of the embodiments are not intended to be limited in this manner.

In an embodiment, an expandable portion of the present disclosure includes a surface that is resilient and puncture resistant. In an embodiment, the surface of the expandable portion is substantially even and smooth. In an embodiment, the surface of the expandable portion is not entirely smooth and may have some small bumps, riblets or convexity/concavity along the length. In an embodiment, the surface of the expandable portion may have ribs, ridges, bumps or other shapes. In an embodiment, the expandable portion has a surface comprising riblets configured to break up surface tension. In an embodiment, the expandable portion has a textured surface which provides one or more ridges that allow grabbing. In an embodiment, abrasively treating the surface of the expandable portion via chemical etching or air propelled abrasive media improves the connection and adhesion between the surface of the expandable portion and the bone. The surfacing significantly increases the amount of surface area that comes in contact with the bone, which may increase friction between the expandable portion and the bone and/or may increase tissue ingrowth into the expandable portion.

FIG. 2 shows a side view of an embodiment of a distal end 114 of the insertion catheter 101 of FIG. 1 of a photodynamic bone stabilization and drug delivery system of the present disclosure. The distal end 114 includes an expandable portion 200 (illustrated in an expanded position) sufficiently designed to stabilize a bone and to deliver at least one additive locally to the endosteal surface of the bone. In an embodiment, the expandable portion 200 is made from a thin-walled, non-compliant material.

In the embodiment illustrated in FIG. 2A, the inner lumen 220 is an internal through hole that passes through the longitudinal axis of the flexible insertion catheter 101 and through a distal end 214 of the expandable portion 200. The through hole 220 is sufficiently designed to pass a light-conducting fiber, configured to pass a cooling medium, and configured for housing and releasing at least one additive. In an embodiment, the cooling medium is sufficiently designed to cool the expandable portion 200 during the curing process. In an embodiment, the cooling medium is sufficiently designed to cool the expandable portion 200 so that the additive remains stable and does not denature.

In an embodiment, the at least one additive is delivered in solution form through the through hole 220 and passes out the distal end 214 of the expandable portion 200 for local delivery to the endosteal surface of the bone. In an embodiment, the at least one additive is delivered in encapsulated form through the through hole 220 and passes out the distal end 214 of the expandable portion 200 for local delivery to the endosteal surface of the bone. In an embodiment, the at least one additive is delivered as a polymer-drug compound and positioned within the through hole 220 to release the additive out the distal end 214 of the expandable portion 200 for local delivery to the endosteal surface of the bone. In an embodiment, the at least one additive is incorporated/impregnated in a scaffold positioned within the through hole 220 to release the additive out the distal end 214 of the expandable portion 200 for local delivery to the endosteal surface of the bone. The polymer-drug compounds and scaffolds provide a mechanism whereby the rate of release and availability of the additive may be regulated so that the quantity of an additive which is released at a particular time at the endosteal surface of the bone is relatively constant and uniform over extended periods of time.

During an embodiment of a procedure for repairing a weakened to fractured long bone, the expandable portion 200 is positioned between bone fragments and light-sensitive liquid is passed through the inner void 110 of the photodynamic bone stabilization and drug delivery system until it reaches the expandable portion 200 and begins to expand or inflate the expandable portion 200. The expandable portion 200 is inflated in situ with light-sensitive liquid to stabilize and reduce the fracture, which can optionally be performed under fluoroscopy. Because the light-sensitive liquid will not cure until illumination with light from the light-conducting fiber, the expandable portion 200 can be inflated and deflated as many times as needed in situ to insure the proper stabilization and reduction of the fracture. Once proper positioning of the expandable portion 200 is determined, the light-conducting fiber is positioned in the through hole 220 of the photodynamic bone stabilization and drug delivery system and activated, to deliver output energy directly to the expandable portion 200 which will polymerize or cure the light-sensitive liquid and stabilize the bone. During use, there is the potential that the in situ curing process of the light-sensitive liquid can cause one or more areas of the expandable portion 200 to experience a temperature rise. To prevent a temperature rise from occurring, a cooling medium can be delivered through the through hole 220 concurrently with the light-conducting fiber, so as to cool the expandable portion 200 during the curing process. After the curing process, at least one additive, such as an antibiotic, a growth factor and/or a bisphosphonate, can be locally delivered to the inner cavity of the bone via the through hole 220 in the expandable portion 200. Additives can be delivered, for example, in solution form, encapsulated in nanoparticles (such as liposomes), encapsulated in microparticles (such as microspheres and microcapsules), as polymer-drug compounds, and incorporated/impregnated into a scaffold. Release of the additive locally to the bone can be immediate or sustained (long-term). Release of the additive locally to the endosteal surface of the bone can last a few hours, a few days, or a few weeks. The expandable portion 200 once hardened, is released from the insertion catheter 101. In an embodiment, after the expandable portion 200 is released, an opening is created at the proximal end of the expandable portion 200 providing an additional site of release of the at least one additive from the through hole 220 of the expandable portion 200. In an embodiment, the through hole 220 is connected to a port in the patient having the hardened expandable portion 200. In an embodiment, the port has been implanted, for example, subcutaneously. In an embodiment, the port is attached to the skin. The port is an entry point that can be used for later infusion of additional additives during the healing process.

In an embodiment, at least one additive may be delivered to the through hole 220 of the expandable portion 200 through an inner lumen of the insertion catheter. In an embodiment, the through hole 220 may be connected to a flexible tube 270 attached to a port 271 as illustrated in FIG. 2B. The port 271 can include an adapter, such a Luer lock, so a syringe can be connected to the port 271 for infusion of additives both before and after implantation of the expandable portion into the body of a patient. In an embodiment, the port 271 can be implanted, for example, subcutaneously. In an embodiment, the port 271 is rested on the surface of the skin. In an embodiment, the port 271 can be used to refill the through hole 220 with additives during the healing process.

Figure 3A:
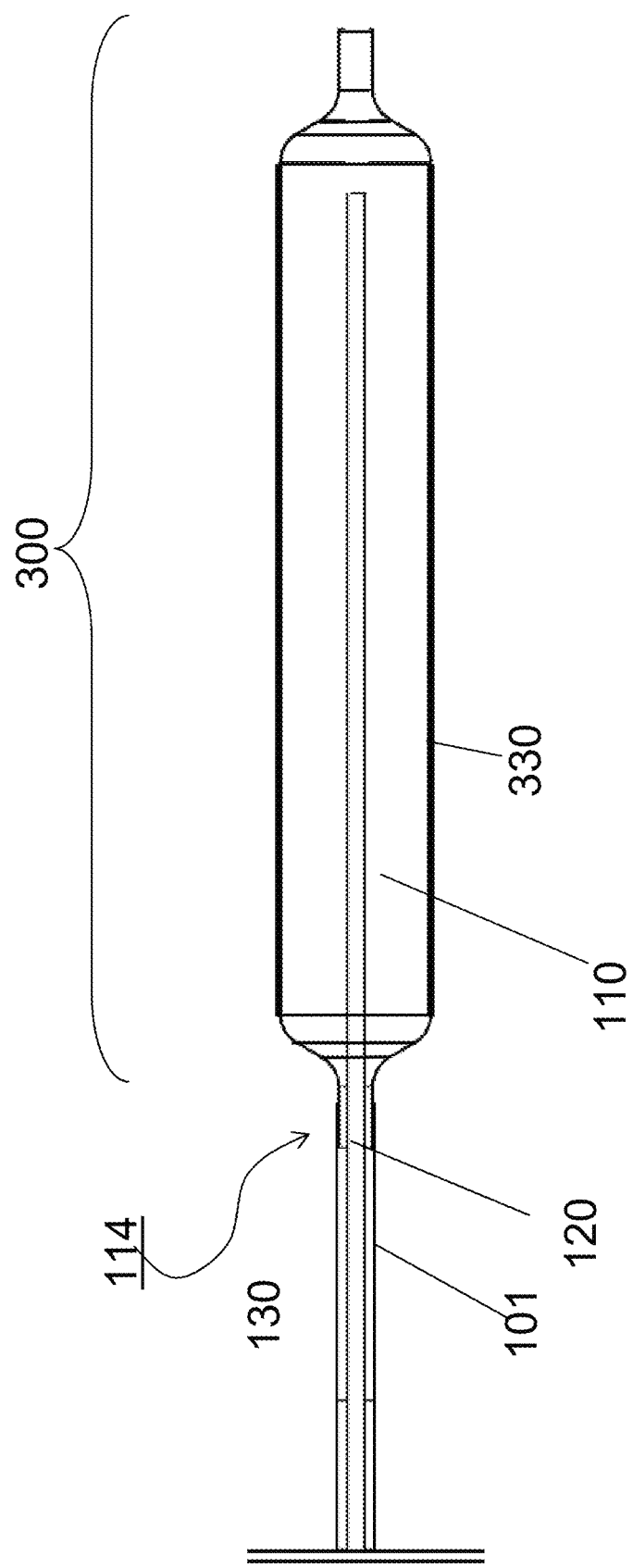
FIG. 3A shows a side view of an embodiment of a distal end of a photodynamic bone stabilization and drug delivery system for repairing a weakened or fractured bone according to the present disclosure. The distal end includes an expandable portion (illustrated in an expanded position) sufficiently designed to stabilize the bone, the expandable portion having an outer surface layer incorporating at least one additive for local delivery of the additive to the bone.

FIG. 3A shows a side view of an embodiment of a distal end 114 of a photodynamic bone stabilization and drug delivery system for repairing a weakened or fractured bone according to the present disclosure. The distal end 114 includes an expandable portion 300 (illustrated in an expanded position) sufficiently designed to stabilize a bone. In an embodiment, the expandable portion 300 is made from a thin-walled, non-compliant material.

In an embodiment, the expandable portion 300 (illustrated in an expanded position) includes an outer surface layer 330 incorporating at least one additive. The outer surface layer 330 may extend along only a section of the expandable portion 300 or along the entire length of the expandable section 300. In an embodiment, the outer surface layer 330 is one which conforms to the shape of the expandable portion 300, i.e. expands with the expandable portion 300 when the expandable portion 300 is expanded and contracts when the expandable portion 300 is deflated. In an embodiment, the outer surface layer 330 is made from a polymer.

In an embodiment, the outer surface layer 330 may include pores (not shown) designed to be filled with the at least one additive. The pores in the outer surface layer 330 may be designed such that, when the expandable portion 300 is collapsed, the pores are closed to effectively retain the at least one additive therein. However, when the expandable portion 300 is expanded, the pores are stretched open to enable the release of the at least one additive from the outer surface layer 330. In another embodiment, the surface of the outer surface layer 330 may be coated with the at least one additive or a matrix containing the at least one additive. In such an embodiment, when the expandable portion 300 is expanded in the medullary cavity of a bone, the outer surface layer 330 may come in contact with a surface of the bone to deposit the at least one additive or a matrix containing the at least one additive thereon.

In an embodiment, the outer surface layer 330 is made from electrospun nanofibers. In an embodiment, the diameter of the nanofibers is in the range of about 2 to about 4000 nanometers. In an embodiment, the diameter of the nanofibers is in the range of about 2 to about 3000 nanometers, and accordingly a large number of nanofibers is present on the outer surface 330 of the expandable portion 300. Accordingly, the electrospun surface constitutes a relatively large reservoir for the additive compared to the weight of the coated expandable portion 300. It should be understood that the term electrospinning comprises a process wherein particles are applied onto a base element which is kept at a certain, preferably constant, electric potential, preferably a negative potential. The particles emerge from a source which is at another, preferably positive potential. The positive and negative potentials may, for example, be balanced with respect to the potential of a surrounding environment, i.e., a room in which the process is being performed. The potential of the base element with respect to the potential of the surrounding atmosphere may be between about −5 and about −30 kV, and the positive potential of the source with respect to the potential of the surrounding atmosphere may be between about +5 and about +30 kV, so that the potential difference between source and base element is between about 10 and about 60 kV.

Nanofibers produced by an electrospinning method are widely used where specific pore characteristics are required. In an embodiment, an expandable portion having an outer surface layer made from electrospun nanofibers has pores that are resistant to cellular infiltration while retaining the ability for small molecules, additives, nutrients and water to pass through. The expandable portion 300 produced by the present disclosure may define a plurality of sections along its length. For example, the sections may have different properties, such as different hardness. Such different properties may be arrived at by employing different fiber-forming materials for different sections and/or by changing production parameters, such as voltage of electrodes in the electrospinning process, distance between high-voltage and low-voltage electrodes, rotational speed of the device (or of a core wire around which the device is manufactured), electrical field intensity, corona discharge initiation voltage or corona discharge current.

In order to improve adhering of the electrospun outer surface layer 330 to the expandable portion 300, the expandable portion body may be covered by an intermediate polymer layer, such as a Ticoflex™ layer, before it is being coated. For example, the intermediate layer may be formed by dip-coating the expandable portion 300. The intermediate layer may alternatively be formed by a polyurethane or by the polymer which is also used for the outer surface layer coating 330.

In an embodiment, the outer surface layer 330 of the expandable portion 300 may constitute a reservoir to additives. The electrospun portions thereof constitute reservoirs for holding additives or constitute a matrix polymer source where the additives is either blocked into the molecule chain or adheres to or surrounds the molecule chain. The expandable portion 300 disclosed herein may carry any appropriate additive, including but not limited to antibiotics, growth factors and bisphosphonates. The electrospun fibers form a polymer matrix of one or more polymers. It should be understood that the outer surface layer 330 made from electrospun fibres, i.e. the polymer matrix, needs not to be the outermost layer of the expandable portion 300, for example a layer of a hydrophilic polymer (e.g. polyacrylic acids (and copolymers), polyethylene oxides, poly(N-vinyl lactams such as polyvinyl pyrrolidone, etc.) may be provided as a coating on the outer surface layer 330 (polymer matrix). Alternatively, a barrier layer may be provided as coating on the outer surface layer 330 (polymer matrix) in order to ensure that contact between the polymer matrix and any intramedullary material is delayed until the expandable portion 300 is in place. The barrier layer may either be formed of a biodegradable polymer which dissolves or disintegrates, or the barrier layer may be disintegrate upon inflation of the expandable portion 300.

The additive may be mixed into a liquid substance from which the outer surface layer 330 is manufactured. In another embodiment, the additive(s) is/are present within the polymer matrix as discrete molecules. Within this embodiment, the additive(s) may be contained in microparticles, such as microspheres and microcapsules. The microparticles may be biodegradable and may be made from a biodegradable polymer such as a polysaccharide, a polyamino acid, a poly(phosphoester) biodegradable polymer, a polymers or copolymers of glycolic acid and lactic acid, a poly(dioxanone), a poly(trimethylene carbonate)copolymer, or a poly(α-caprolactone) homopolymer or copolymer. Alternatively, the microparticles may be non-biodegradable, such as amorphous silica, carbon, a ceramic material, a metal, or a non-biodegradable polymer. The microparticles may be in the form of microspheres that encapsulate the additive, such as the antibiotic, growth factor or bisphosphonate.

Figure 3B:
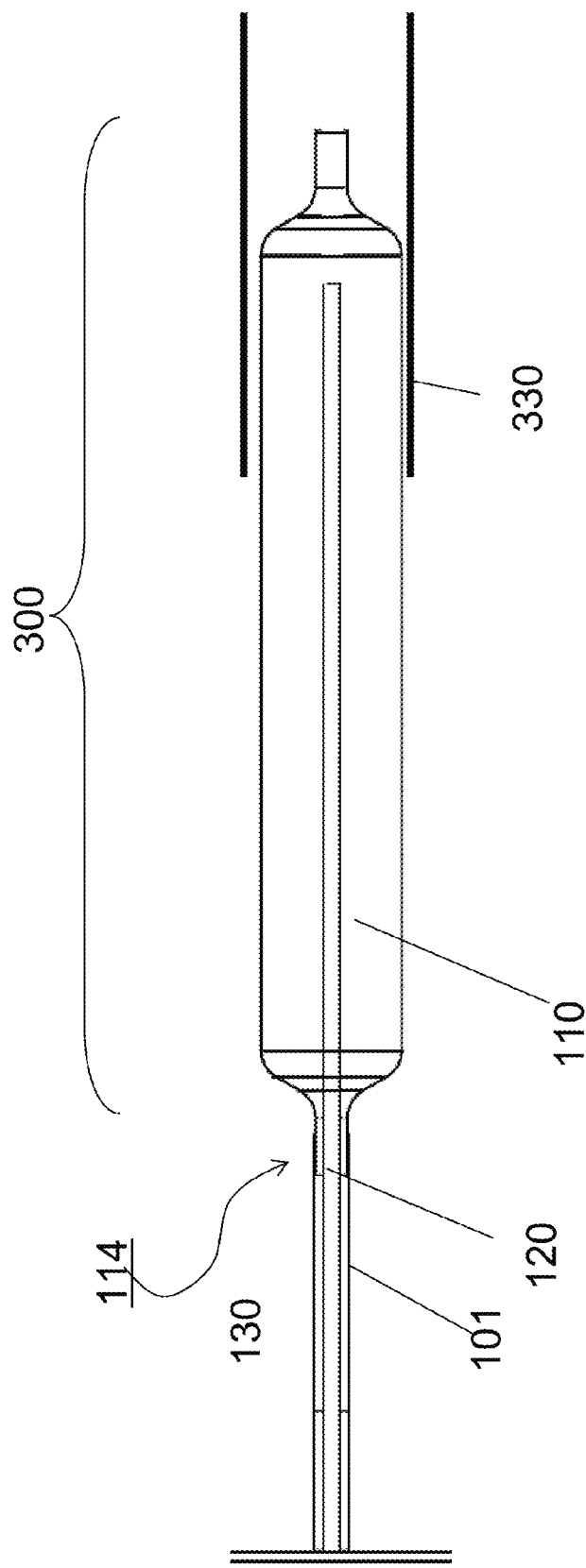
FIG. 3B shows a side view of an embodiment of a distal end of a photodynamic bone stabilization and drug delivery system for repairing a weakened or fractured bone according to the present disclosure. The distal end includes an expandable portion (illustrated in an expanded position) sufficiently designed to stabilize the bone. A separate micro porous flexible tube incorporating various additives may be slipped over the expandable portion for local delivery of the additive to the bone.

In an embodiment, a separate micro porous flexible tube incorporating various additives is sufficiently designed to be slipped over an expandable portion of the present disclosure. FIG. 3B shows an embodiment of a micro porous flexible tube 350 being slid over the expandable portion 300. Benefits of using the micro porous flexible tube 350 include, but are not limited to, the delivery of the additive(s) at a physician-selected location and/or point in time. Providing the micro porous flexible tube 350 separately from the expandable portion 300 can enable placement of the tube 350 at any position over the expandable portion 300. In an embodiment, the position of the tube 350 relative to the site of repair and/or relative to the expandable portion 300 can be adjusted after the implantation of the expandable portion 300. In an embodiment, the position of the tube 350 the expandable portion 300 relative to the site of repair can be adjusted, so as to maximize the benefit of the at least one additive released from tube 350. In an embodiment, the porous tube 350 can be slid over the expandable portion 300 while the expandable portion 300 is deflated and the porous tube 350 can be expanded by the expansion of the expandable portion 300.

Figure 4A:
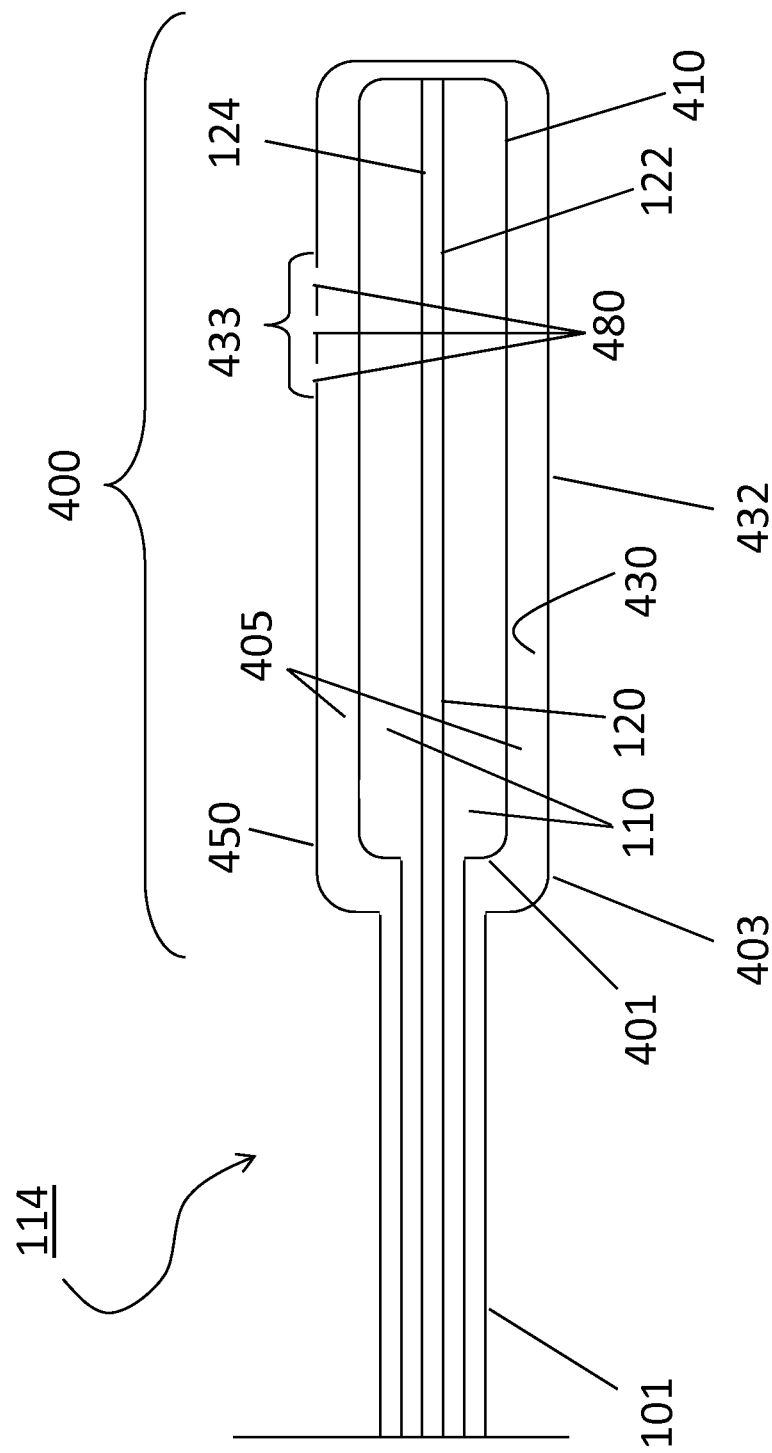
FIG. 4A shows a side view of an embodiment of a distal end of a photodynamic bone stabilization and drug delivery system for repairing a weakened or fractured bone according to the present disclosure. The distal end includes an expandable portion (illustrated in an expanded position) having an inner expandable portion sufficiently designed to stabilize the bone, the inner expandable portion surrounded by an outer expandable portion sufficiently designed to release at least one additive, housed between the inner expandable portion and the outer expandable portion, locally to the bone.

Accordingly, various micro porous flexible tubes having various properties or incorporating various additives may be inexpensively manufactured and slipped over an expandable portion. The micro porous flexible tube may be formed by providing a core element, such as a mandrel, onto which the nanofibers are deposited by electrospinning as the mandrel is continuously rotated. The micro porous flexible tube may be formed from a porous fabric FIG. 4A shows a side view of an embodiment of a distal end 114 of a photodynamic bone stabilization and drug delivery system for repairing a weakened or fractured bone according to the present disclosure, in which an expandable portion 400 (illustrated in an expanded position) is a double wall balloon, having an inner wall 401 and an outer wall 403. The inner wall 401 and the outer wall 403 define an inner expandable portion 410 sufficiently designed to receive a light sensitive liquid to stabilize the bone, and an outer expandable portion 450 sufficiently designed to house and release at least one additive. In an embodiment, the inner expandable portion 410 is surrounded by the outer expandable portion 450. In the embodiment illustrated in FIG. 4A, the inner lumen 120 is sufficiently designed to pass a light-conducting fiber which, when activated, cures the light-sensitive liquid monomer. The inner expandable portion 410 includes the inner void 110 between an outer surface of the inner lumen 120 and an inner surface of the inner wall 401. The inner void 110 is sufficiently designed to be filled with a light sensitive liquid. The outer expandable portion 450 includes a second inner void 405 between an outer surface of the inner wall 401 and an inner surface 430 of the outer wall 403. The second inner void 405 is sufficiently designed to house at least one additive.

In an embodiment, a surface of an expandable balloon portion may be textured. In an embodiment, the outer surface of the inner wall 401 of the inner expandable balloon portion 410, the inner surface of the outer wall 403 of the outer expandable balloon portion 450 or both surfaces may be textured, as illustrated in FIG. 4B. The textured surfaces may prevent capillary adhesion between the surfaces of the inner wall 401 and the outer wall 403 during infusion of a liquid, such as a liquid carrying an additive. In an embodiment, prevention of capillary adhesion may facilitate the addition of the additive into the second inner void 405. The textured surface may be provide in a form selected from at least one of bumps, riblets, ribs, ridges or other shapes.

Figure 4C:
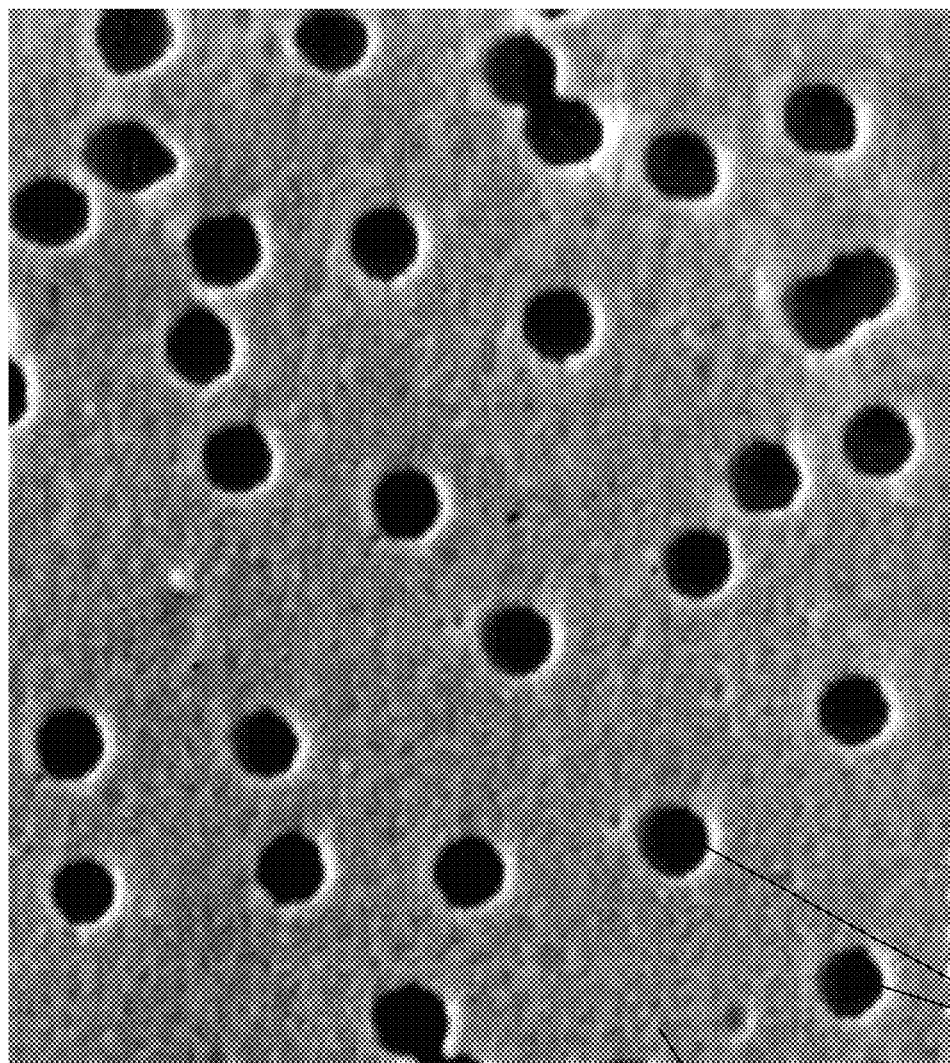
FIG. 4C is a micrograph showing a micro-perforated surface of the outer expandable portion of the photodynamic bone stabilization and drug delivery system of FIG. 4A.

In an embodiment, the inner wall 401 is formed from a non-permeable, pliable, resilient, conformable, compliant, and strong material, including but not limited to urethane, polyethylene terephthalate (PET), nylon elastomer and other similar polymers. In an embodiment, the outer wall 403 is formed from a pliable, resilient, conformable, compliant, and strong material, including but not limited to urethane, polyethylene terephthalate (PET), nylon elastomer and other similar polymers. To enable the release of the at least one additive from the second inner void 405, at least a section of the outer wall 403, referred herein as a porous section 433, has holes or pores 480, extending from an inner surface 430 to an outer surface 432 the outer wall 403, as illustrated in FIG. 4C. In an embodiment, the porous section 433 may be formed from a non-porous polymer and the pores 480 may be made in the outer expandable portion 450 by, for example, laser drilling, mechanical punching, mechanical drilling, ion-bean drilling, using a hot wire or any other conventional method known in the art.

Additionally or alternatively, the porous section 433 may be formed from a porous polymer material. In an embodiment, at least a portion of the outer wall is formed from a porous polymer material. Examples of natural porous polymers include gelatin, fibrin, collagen, elastin, hyaluronic acid, chondroitin sulfate, dermatan sulfate, heparin sulfate, heparin, cellulose, chitin, chitosan, mixtures or copolymers thereof, or a wide variety of others typically disclosed as being useful in implantable medical devices. Examples of synthetic porous polymers include silicone, polyurethane, polysulfone, polyethylene, polypropylene, polyamide, polyester, polycarboxylic acids, polyvinylpyrrolidone (PVP), maleic anhydride polymers, polyamides, polyvinyl alcohols (PVA), polyethylene oxides, polyacrylic acid polymers, polytetrafluoroethylene, polyhydroxyethylmethacrylic acid (pHEMA), polyaminopropylmethacrylamide (pAPMA), polyacrylamido-2-methylpropanesulfonic acid (pAMPS), polyacrylamide, polyacrylic acid, mixtures or copolymers thereof, or a wide variety of others typically disclosed as being useful in implantable medical devices. Additional examples of synthetic porous polymers include biodegradable synthetic porous polymers, such as polyglycolic acid, polylactic acid, polydiaxonone, poly(,-caprolactone), polyanhydrides, poly(3-hydroxybutyrate), poly(ortho esters), poly(amino acids), polyiminocarbonates, and mixtures or copolymers thereof. The porosity of these materials may be varied by known techniques during the manufacturing process. In another embodiment, pores may be made along at least a portion of the outer wall by, for example, laser drilling, mechanical punching, mechanical drilling, ion-bean drilling, using a hot wire or any other conventional method known in the art.

In one embodiment, as illustrated in FIG. 4B, the porous section 433 may extend along a section of the outer expandable portion 450. Alternatively, the porous section 433 may extends along the entire lengths of the outer expandable portion 450. The porous section 433, and the pores 480, may be sufficiently designed to release the at least one additive from the second inner void 405 to the endosteal surface of the bone at a pre-determined flow. As used herein, the terms "pre-determined flow" and "flow" may refer to the rate of flow, profile of flow, distribution of flow along the outer expandable portion 450, the time period over which the at least one additive is delivered or combinations thereof. To achieve the pre-determined flow of the at least one additive from the second inner void 405, the porosity of outer expandable portion 450 may be varied by varying the quantity, size and shape of the pores 480, as well as the length, position and number of porous sections. In an embodiment, the size and shape of the pores 480 in the porous section 433 may be substantially uniform. In this manner, the flow of the at least one additive through the porous section 433 may be substantially uniform. In another embodiment, a particular region at the site of implantation of the expandable portion 400 may require a higher concentration of the at least one additive than other regions, and thus the size and shape of the pores 480 in the porous section 433 may be substantially non-uniform throughout the porous section 433. Alternatively or additionally, the length, position or number of porous sections may be varied circumferentially and axially along the outer expandable portion 450 to achieve a substantially uniform or substantially non-uniform flow of the at least one additive from the second inner void 405.

The pores 480 may be of any size and shape as needed to maintain the pre-determined flow of the at least one additive from the outer expandable portion 450. The pores 480 may be straight or tortuous, and may be, in various embodiments, oval, circular, or elliptical. The pores 480 may range in size from less than 1 mm to several microns in diameter. Hundreds of thousands or even millions of pores 480 of this size can be placed in the porous section 433. Such a design permits pore size to be precisely controlled, enabling very small amounts of an additive (e.g., an antibiotic, a bone growth factor or a bisphosphonate) to be infused over an accurately defined area over a selected time-frame. In an embodiment, use of the porous section 433 in the outer expandable portion 450 enables a physician to localize the additive and avoid systemic intravenous administration.

In an embodiment, the pore size of the porous section 433 can be controlled by using an electrospinning method for the production of the porous section 433. By changing the non-woven geometry (diameter of fiber, surface properties of fibers, packing density, thickness of film) the rheology of the fluid flow through the porous section 433 can be changed. In an embodiment, the porous section 433 having the pores 480 may be resistant to cellular infiltration (i.e. a barrier film) that retains the ability for small molecules, nutrients and water to pass through.

Figure 4D:
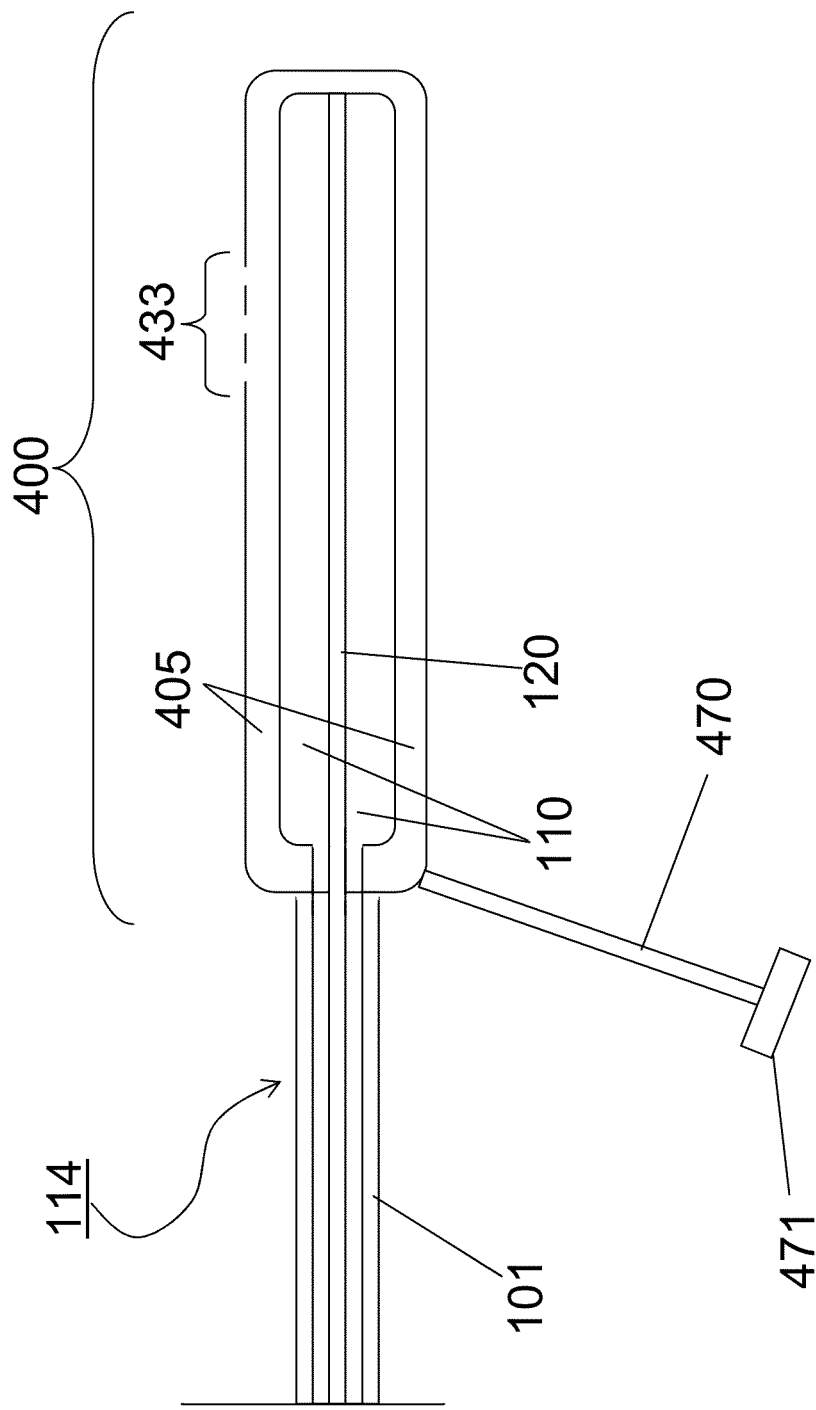
FIG. 4D shows a side view of an embodiment of a distal end of a photodynamic bone stabilization and drug delivery system for repairing a weakened or fractured bone according to the present disclosure. The distal end includes an expandable portion (illustrated in an expanded position) having an inner expandable portion sufficiently designed to stabilize the bone, the inner expandable portion surrounded by an outer expandable portion sufficiently designed to release at least one additive, housed between the inner expandable portion and the outer expandable portion, locally to the bone. The expandable portion is connected to a flexible tube with a port.

In an embodiment, a photodynamic bone stabilization and drug delivery system of the present disclosure is used to deliver drugs from outside of the body into the intramedullary canal of a bone. In an embodiment, the drugs are site specific deliverables. In an embodiment, the second inner void 405 may be connected to a flexible tube 470 attached to a port 471 as illustrated in FIG. 4D. The port 471 can include an adapter, such a Luer lock, so a syringe can be connected to the port 471 for infusion of additives both before and after implantation of the expandable portion into the body of a patient. In an embodiment, following the implantation of the expandable portion 400 into the medullary cavity, the port 471 can be implanted, for example, subcutaneously. In an embodiment, following the implantation of the expandable portion 400 into the medullary cavity, the port 471 is rested on the surface of the skin. In an embodiment, the port 471 can be used to refill the second inner void 405 of the implanted expandable portion 400 with additives during the healing process. In an embodiment, following the implantation of the expandable portion 400 into the medullary cavity, physician specified drugs may be delivered to the to the second inner void 405 from an external storage reservoir via a pump connected to the port 471. In an embodiment, the flexible tube 470 is removably attached to the second inner void 405, such that, following the completion of the physician specified drug treatment, the flexible tube 470 can be detached from the second inner void 405, if so desired, without disruption of the medullary cavity.

Figure 5:
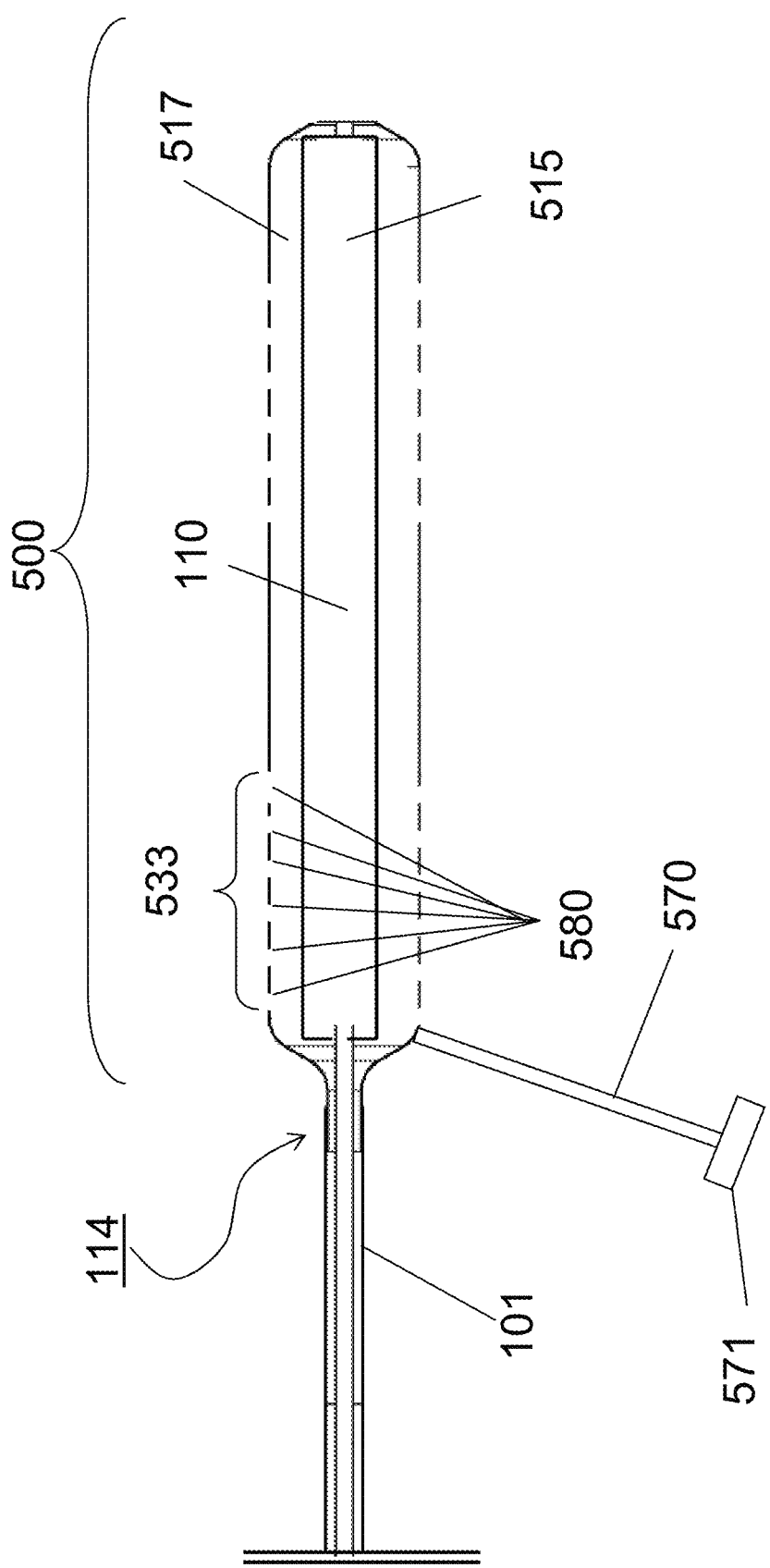
FIG. 5 shows a side view of an embodiment of a distal end of a photodynamic bone stabilization and drug delivery system for repairing a weakened or fractured bone according to the present disclosure. The distal end includes an expandable portion (illustrated in an expanded position) having an outer wall with a porous section.

FIG. 5 shows a side view of an embodiment of a distal end 114 of a photodynamic bone stabilization and drug delivery system for repairing a weakened or fractured bone according to the present disclosure. The distal end 114 includes an expandable portion 500 (illustrated in an expanded position) that can be used to deliver at least one additive locally to a site of interest. In an embodiment, the expandable portion 500 is sufficiently designed to be inserted into the medullary cavity of a bone and to deliver at least one additive to the endosteal surface of the bone at a pre-determined flow. In an embodiment, the expandable portion 500 is a single wall balloon made from a thin-walled, non-compliant material. In an embodiment, as illustrated n FIG. 5, the expandable portion 500 may be a double wall balloon, with properties similar to those of the expandable portion 400. In an embodiment, the expandable portion 500 may include an inner expandable portion 515 sufficiently designed to maintain a first fluid therein and an outer expandable portion 517, surrounding the inner expandable portion and sufficiently designed to house and release at least one additive.

To enable the release of the at least one additive from the expandable portion 500, at least a section of the outer wall 501, referred herein as a porous section 533, has pores 580 extending from the inner surface 530 to the outer surface 532 of the outer wall 501. The porous section 533 may, in some embodiments, extend along a section of the outer wall 501, while, in other embodiments, the porous section 533 may extend along the entire lengths of the outer wall 501. The porous section 533 may have properties similar to those of the porous section 433, described as above. In an embodiment, at least one additive may be delivered to the expandable portion 500 through an inner lumen of the insertion catheter In an embodiment, a photodynamic bone stabilization and drug delivery system of the present disclosure is used to deliver drugs from outside of the body into the intramedullary canal of a bone. In an embodiment, the drugs are site specific deliverables. In an embodiment, the expandable portion 500 may be connected to a flexible tube 570 attached to a port 571 as illustrated in FIG. 5. The port 571 can include an adapter, such a Luer lock, so a syringe can be connected to the port 571 for infusion of additives both before and after implantation of the expandable portion into the body of a patient. In an embodiment, following the implantation of the expandable portion 500 into the medullary cavity, the port 571 can be implanted, for example, subcutaneously. In an embodiment, following the implantation of the expandable portion 500 into the medullary cavity, the port 571 is rested on the surface of the skin. In an embodiment, the port 571 can be used to refill the implanted expandable portion 500 with additives during the healing process. In an embodiment, following the implantation of the expandable portion 500 into the medullary cavity, physician specified drugs may be delivered to the to the expandable portion 500 from an external storage reservoir via a pump connected to the port 571. In an embodiment, the flexible tube 570 is removably attached to the expandable portion 500, such that, following the completion of the physician specified drug treatment, the flexible tube 570 can be detached from the expandable portion 500, if so desired, without disruption of the medullary cavity.

Figure 6:
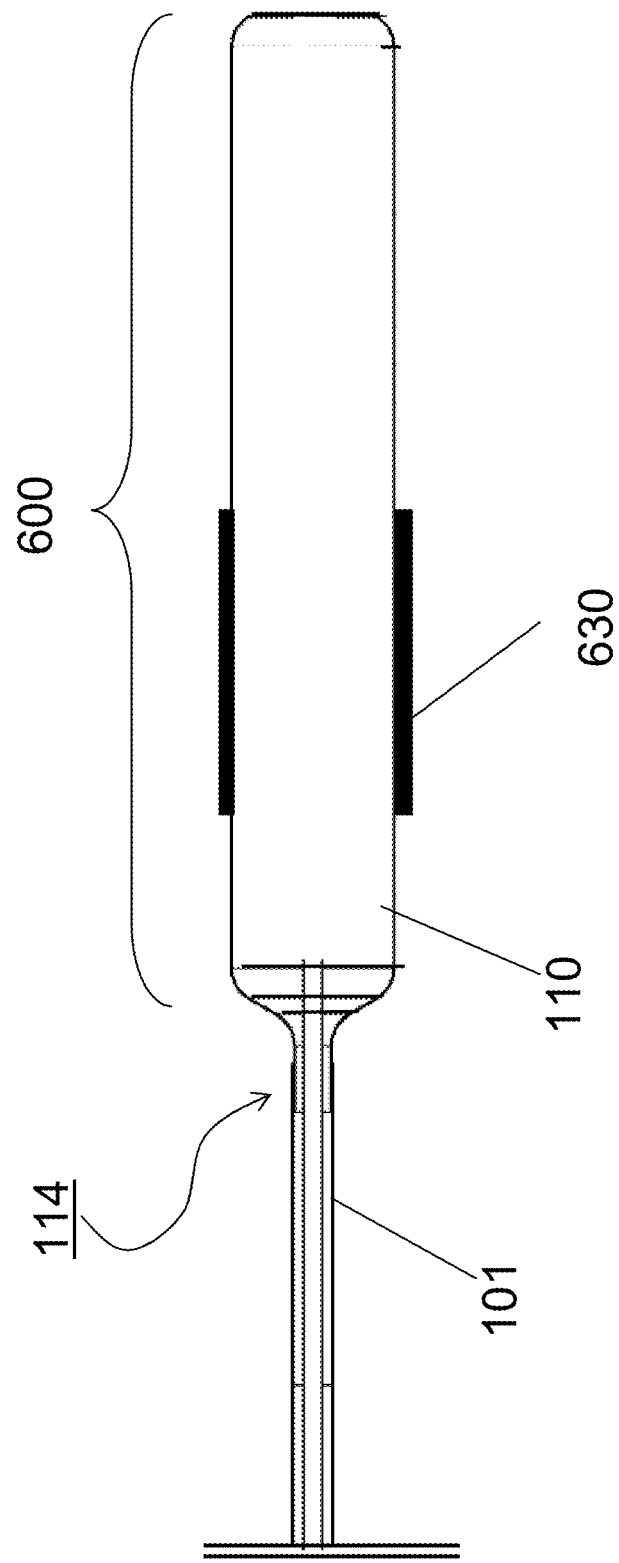
FIG. 6 shows a side view of an embodiment of a distal end of a photodynamic bone stabilization and drug delivery system for repairing a weakened or fractured bone according to the present disclosure. The distal end includes an expandable portion (illustrated in an expanded position) having a surface layer incorporating at least one additive.

FIG. 6 shows a side view of an embodiment of a distal end 114 of a photodynamic bone stabilization and drug delivery system for repairing a weakened or fractured bone according to the present disclosure. The distal end 114 includes an expandable portion 600 (illustrated in an expanded position) having an outer wall 610, which defines the inner void 110. In an embodiment, the expandable portion 600 is made from a thin-walled, non-compliant material. The expandable portion 600 is sufficiently designed to be inserted into the medullary cavity of a bone and to deliver at least one additive to the endosteal surface of the bone at a pre-determined flow. To that end, the expandable portion 600 may include a surface layer 630 incorporating at least one additive. The outer surface layer 630 may extend along only one or more sections of the outer wall 601 or along the entire length of the outer wall 601. The outer surface layer 630 may have properties similar to those of the outer surface layer 330, as described above. In particular, the outer surface layer 630 may, in an embodiment, include pores (not shown) designed to be filled with the at least one additive. The pores in the outer surface layer 630 may be designed such that, when the expandable portion 600 is collapsed, the pores are closed to effectively retain the at least one additive therein. However, when the expandable portion 600 is expanded, the pores 680 are stretched open to enable the release of the at least one additive from the outer surface layer 630. In an embodiment, the expandable portion 600 may be expanded by delivering a saline or a similar solution into the inner void 110. In an embodiment, the outer surface layer 630 may be a separate micro porous flexible tube sufficiently designed to be slipped over the expandable portion 600, as described with respect to the embodiment of the photodynamic bone stabilization and drug delivery system of the present disclosure illustrated in FIG. 3B.

Figure 7:
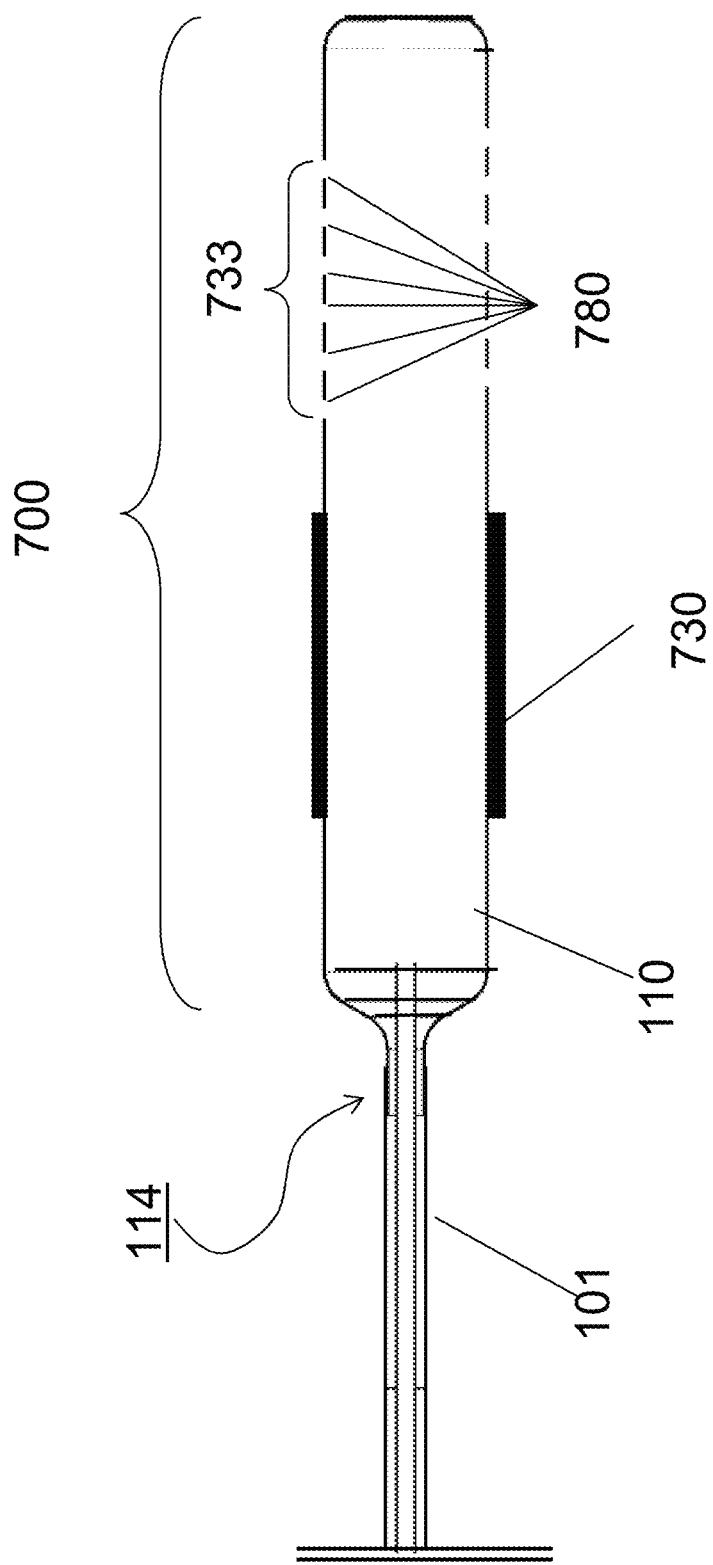
FIG. 7 shows a side view of an embodiment of a distal end of a photodynamic bone stabilization and drug delivery system for repairing a weakened or fractured bone according to the present disclosure. The distal end includes an expandable portion (illustrated in an expanded position) having an outer wall with a porous section and a surface layer incorporating at least one additive.

FIG. 7 shows a side view of an embodiment of a distal end 114 of a photodynamic bone stabilization and drug delivery system for repairing a weakened or fractured bone according to the present disclosure. The distal end 114 includes an expandable portion 700 (illustrated in an expanded position) having an outer wall 710, which defines the inner void 110. In an embodiment, the expandable portion 700 is made from a thin-walled, non-compliant material. The expandable portion 700 is sufficiently designed to be inserted into the medullary cavity of a bone and to deliver at least one additive to the endosteal surface of the bone at a pre-determined flow. For that reason, in the embodiment shown in FIG. 7, the outer wall 710 may include both a porous section 733 and a outer surface layer 730. The porous section 733 and the outer surface layer 730 may have properties similar to those of the porous sections 433 and 533 and outer surface layers 330 and 630, respectively. The porous section 733 and the outer surface layer 730 may be used to deliver the same or different additives.

Figure 8A:
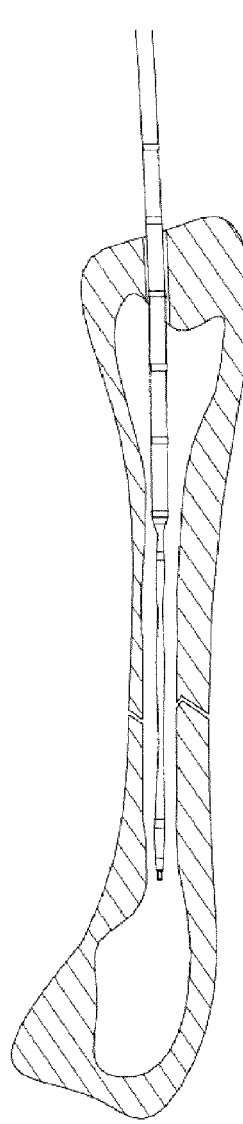
Figure 8B:
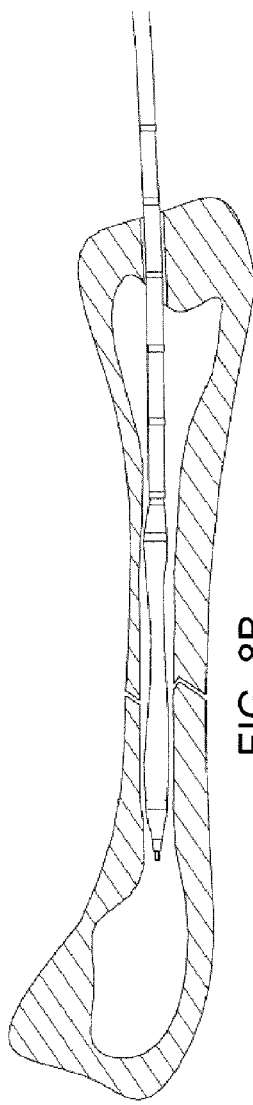
Figure 8C:
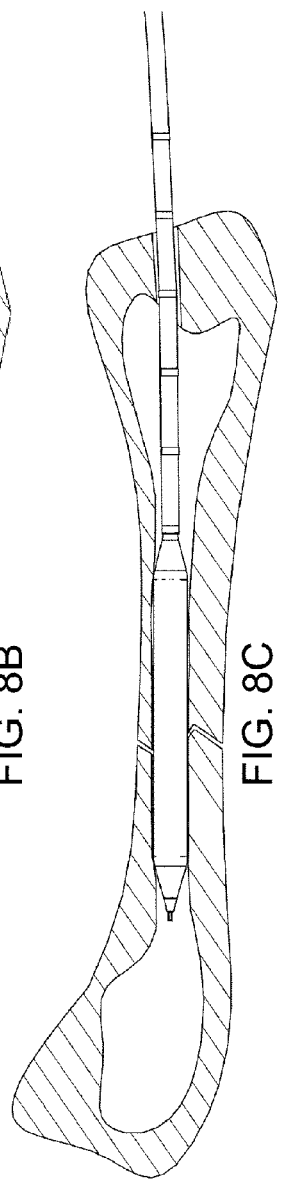

FIGS. 8A-8D illustrate an embodiment of a procedure for repairing a weakened or fractured bone using a photodynamic bone stabilization and drug delivery system of the present disclosure. As illustrated in FIG. 8A, a procedure for repairing a weakened or fractured bone includes positioning the expandable portion between bone fragments. In an embodiment, the expandable portion spans multiple bone fragments. Once the expandable portion is positioned, light-sensitive liquid monomer is passed through the inner void of the photodynamic bone stabilization system until it reaches the expandable portion and begins to expand or inflate the expandable portion, as shown in FIG. 8B. The expandable portion is inflated in situ with light-sensitive liquid monomer to stabilize and reduce the fracture, which can optionally be performed under fluoroscopy. Because the light-sensitive liquid monomer will not cure until illumination with light from the light-conducting fiber, the expandable portion can be inflated and deflated as needed in situ to insure the proper stabilization and reduction of the fracture. Once proper positioning of the expandable portion is determined, the light-conducting fiber is introduced into the inner lumen of the expandable portion and activated, to deliver output energy to the expandable portion which will polymerize or cure the light-sensitive liquid monomer, as shown in FIG. 8C.

Figure 8D:
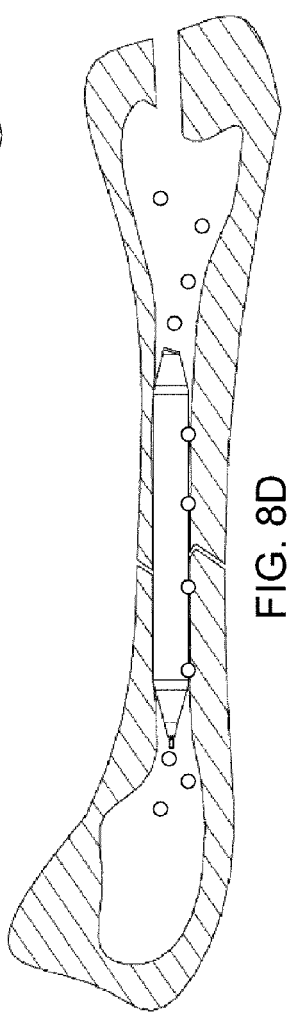

FIG. 8D shows the hardened expandable portion positioned within the weakened or fractured bone after the catheter has been released. At least one additive (shown as dots) is released from the expandable portion near the endosteal surface of the bone. In an embodiment, the expandable portion includes a single thin-walled, non-compliant, expandable portion with an internal through hole that extends past a distal surface of the expandable portion for local delivery of at least one additive to the bone. In an embodiment, the expandable portion includes a single thin-walled, non-compliant, expandable portion having an outer surface layer, the outer surface layer being made from electrospun nanofibers and incorporating at least one additive for local delivery of the additive to the bone. In an embodiment, the expandable portion includes two thin-walled, non-compliant, expandable portions, wherein an inner expandable portion is sufficiently designed to stabilize the bone, and wherein an outer expandable portion sufficiently designed to release at least one additive housed between the inner expandable portion and the outer expandable portion. As illustrated in FIG. 8E, in an embodiment, the expandable portion can be connected to a flexible tube 801 that is connected to a port 810. In an embodiment, the port can be implanted, for example, subcutaneously. In an embodiment, the port is attached to the skin 820. The port is an entry point that can be used for refilling the expandable portion with additional additives during the healing process.

In an embodiment, a method for repairing a fractured bone in a patient using a photodynamic bone stabilization system sufficiently designed to control temperature rise that may occur during use includes: a minimally invasive incision is made through a skin of the patient to expose the fractured bone. The incision may be made at the proximal end or the distal end of the fractured bone to expose a bone surface. Once the bone surface is exposed, it may be necessary to retract some muscles and tissues that may be in view of the fractured bone. At least a first proximal access hole is formed in the fractured bone by drilling or other methods known in the art. The first proximal access hole extends through a hard compact outer layer of the fractured bone into the relatively porous inner or cancellous tissue. For bones with marrow, the medullary material should be cleared from the medullary cavity prior to insertion of the insertion catheter. Marrow is found mainly in the flat bones such as hip bone, breast bone, skull, ribs, vertebrae and shoulder blades, and in the cancellous material at the proximal ends of the long bones like the femur and humerus. Once the medullary cavity is reached, the medullary material including air, blood, fluids, fat, marrow, tissue and bone debris should be removed to form a void. The void is defined as a hollowed out space, wherein a first position defines the most distal edge of the void with relation to the penetration point on the bone, and a second position defines the most proximal edge of the void with relation to the penetration site on the bone. The bone may be hollowed out sufficiently to have the medullary material of the medullary cavity up to the cortical bone removed. An introducer sheath may be introduced into the bone via the first access hole and placed between bone fragments of the bone to cross the location of a fracture. The introducer sheath may be delivered into the lumen of the bone and crosses the location of the break so that the introducer sheath spans multiple sections of bone fragments. The expandable portion of the insertion catheter, is delivered through the introducer sheath to the site of the fracture and spans the bone fragments of the bone. Once the expandable portion is in place, the guidewire may be removed. The location of the expandable portion may be determined using at least one radiopaque marker which is detectable from the outside or the inside of the bone. Once the expandable portion is in the correct position within the fractured bone, the introducer sheath may be removed. A delivery system housing a light-sensitive liquid is attached to the proximal end of the insertion catheter. The light-sensitive liquid is then infused through an inner void in the insertion catheter and enters the expandable portion. This addition of the light-sensitive liquid within the expandable portion causes the expandable portion to expand. As the expandable portion is expanded, the fracture is reduced.

Once orientation of the bone fragments are confirmed to be in a desired position, the light-sensitive liquid may be cured within the expandable portion, such as by illumination with a visible emitting light source. In an embodiment, visible light having a wavelength spectrum of between about 380 nm to about 780 nm, between about 400 nm to about 600 nm, between about 420 nm to about 500 nm, between about 430 nm to about 440 nm, is used to cure the light-sensitive liquid. In an embodiment, the addition of the light causes the photoinitiator in the light-sensitive liquid, to initiate the polymerization process: monomers and oligomers join together to form a durable biocompatible crosslinked polymer. In an embodiment, the cure provides complete 360 degree radial and longitudinal support and stabilization to the fractured bone. After the light-sensitive liquid has been hardened, the light-conducting fiber can be removed from the insertion catheter.

An additive, such as an antibiotic, a growth factor and/or a bisphosphonate, can be locally delivered to the bone via the expandable portion. In an embodiment, an additive is delivered at a rate calculated not to increase intramedullary pressure. In an embodiment, such as that illustrated in the embodiment shown and described with regard to FIG. 2, the additive is delivered to the through hole 220 where it can be released (via the distal end) into the intramedullary space of the bone. In an embodiment, such as that illustrated in the embodiment shown and described with regard to FIG. 3, the additive is delivered to the intramedullary space of the bone via the outer surface layer 330. In an embodiment, such as that illustrated in the embodiment shown and described with regard to FIG. 4A, the additive is delivered to the intramedullary space of the bone via the holes 480 in the outer expandable portion 450.

The expandable portion once hardened, may be released from the insertion catheter. The hardened expandable portion remains in the fractured bone, and the insertion catheter is removed. In an embodiment, the outer surface of the hardened expandable portion makes contact with the cortical bone.

In an embodiment, the expandable portion 400 placed in the medullary cavity enables local, site specific delivery of physician specified additives to the medullary cavity from outside of the body. In general, local, site-specific delivery requires a lower dosage of drug than if the same drug was administered systemically. The local, site-specific delivery can produce desired effects by achieving sufficiently high concentration at the target site, while minimizing systemic concentration of the drug. In an embodiment, the second inner void 405 of the photodynamic bone stabilization system of the present disclosure may be filled with at least one additive, which is delivered locally within the medullary cavity following the implantation of the photodynamic bone stabilization system of the present disclosure into the medullary cavity.

In an embodiment, a photodynamic bone stabilization and drug delivery system of the present disclosure is used to deliver physician specified drugs and agents locally into the intramedullary canal from a site external to the intramedullary canal via a conductive catheter fluidly connected to an expandable portion of the system, wherein the conductive catheter can be disconnected from the system without entering the intramedullary canal. In an embodiment, such as illustrated in FIG. 4D, the flexible tube 470 is in fluid communication with the second inner cavity 405 at one end and with the port 471 located outside the medullary cavity at the opposite end, such that the at least one additive may be delivered to the second inner void 405 from outside the intramedullary canal. In an embodiment, the port 471 is implanted subcutaneously or on the surface of the patient skin and the at least one additive may be delivered to the second inner void 405 through the tube 470 from an external drug reservoir by a pump connected to the port 471. In an embodiment, the concentration or combination of the at least one additive delivered to the intramedullary canal from the external reservoir can be changed at any time during the healing process as determined by a physician. In another embodiment, the at least one additive in the external reservoir can be refilled to provide sustained delivery of the at least one additive to the medullary cavity. In an embodiment, the tube 470 and the port 471 can be disconnected from the expandable portion 400 when no longer needed without further disruption or intervention to the intramedullary canal.

In an embodiment, a method for a local delivery of at least one additive, such as an antibiotic, a growth factor and/or a bisphosphonate, to the medullary cavity of a bone is provided. Initially, an embodiment of the photodynamic bone stabilization system of the present disclosure, such as the embodiments illustrated in FIG. 5, may be positioned in the medullary space of the bone, as described above. Once in the medullary cavity of the bone, the at least one additive may be locally delivered into the medullary cavity from the expandable portion 500 through the porous section 533.

In an embodiment, the expandable portion 500 is used to deliver physician specified drugs and agents locally into the intramedullary canal from a site external to the intramedullary canal via a conductive catheter fluidly connected to an expandable portion of the system, wherein the conductive catheter can be disconnected from the system without entering the intramedullary canal. In an embodiment, the flexible tube 570 is in fluid communication with the expandable portion 500 at one end and with the port 571 located outside the medullary cavity at the opposite end, such that the at least one additive may be delivered to the expandable portion 500 from outside the intramedullary canal. In an embodiment, the port 571 is implanted subcutaneously or on the surface of the patient skin and the at least one additive may be delivered to the expandable portion 500 through the tube 570 from an external drug reservoir by a pump connected to the port 571. In an embodiment, the concentration or combination of the at least one additive delivered to the intramedullary canal from the external reservoir can be changed at any time during the healing process as determined by a physician. In another embodiment, the at least one additive in the external reservoir can be refilled to provide sustained delivery of the at least one additive to the medullary cavity. In an embodiment, the tube 570 and the port 571 can be disconnected from the expandable portion 500 when no longer needed without further disruption or intervention to the intramedullary canal.

In an embodiment, a photodynamic bone stabilization system of the present disclosure is sufficiently designed to selectively stiffen an expandable portion of the system during use. In an embodiment, a photodynamic bone stabilization system of the present disclosure includes an expandable portion having a plurality of stiffening members. In an embodiment, the plurality of stiffening members are disposed along the length of the expandable portion. In an embodiment, the plurality of stiffening members are disposed along the length of an outer surface of the expandable portion. In an embodiment, the plurality of stiffening members are disposed along the length of an inner surface of the expandable portion. The stiffening members can be secured to the expandable portion in a variety of ways. For example and not limitation, the stiffening members can be secured to an adapter, e.g., luer, hub, manifold, or a reinforcement or filler material, or support member. Alternatively, the stiffening members can be secured to the expandable portion by way of an engagement member. In this manner, an engagement member can be secured to the surface of the expandable portion such that a space or cavity is defined for engaging the stiffening members. In an embodiment, the expandable portion includes a plurality of stiffening members configured to control or vary axial flexibility along a length of the expandable portion. In an embodiment, the expandable portion includes a plurality of stiffening members that can be disposed radially and/or axially.

In an embodiment, the stiffening members or metallic pieces may protrude or extend from the expandable portion such that the metallic pieces extend beyond the diameter of the expandable portion. In an embodiment, stiffening members or metallic pieces may be situated within the expandable portion such that the diameter of the expandable portion may be substantially maintained. In an embodiment, stiffening members or metallic pieces may be integral with the expandable portion such that the expandable portion and the stiffening members are contiguous with one another. In an embodiment, stiffening members or metallic pieces may be attached, coupled, covered, sheathed, or otherwise connected to the expandable portion. In an embodiment, the stiffening members or metallic pieces may be contiguous with one another so as to form one structure around the expandable portion. In an embodiment, the stiffening members or metallic pieces can be separate and distinct so as to form multiple structures around the expandable portion. In an embodiment, the stiffening members or metallic pieces are circumferentially connected to one another at a distal end and a proximal end forming end plates. In an embodiment, the end plates help maintain the structure of the stiffening members or metallic pieces when the expandable portion is expanded.

In an embodiment, the stiffening members or metallic pieces may alter or change their configuration under a temperature change. In an embodiment, the metallic pieces expand outwards against the bone at the site of fracture. In an embodiment, the metallic pieces can expand to increase the strength of the hardened expandable potion. In an embodiment, the metallic pieces can contract to increase the strength of the hardened expandable potion. In an embodiment, an inner surface of the metallic pieces (those surfaces that are in contact with the external circumferential surface of the expandable portion) are polished to increase internal reflection of the light from the light-conducting fiber. In an embodiment, the metallic pieces are sufficiently designed to be load-bearing shapes. In an embodiment, the metallic pieces have a low profile and can handle large loads. In an embodiment, the metallic pieces may produce a greater amount of force on a large area than a small area. In an embodiment, the metallic pieces may produce a greater amount of force in a tight or narrow space that in a shallow or open space.

Figure 9:
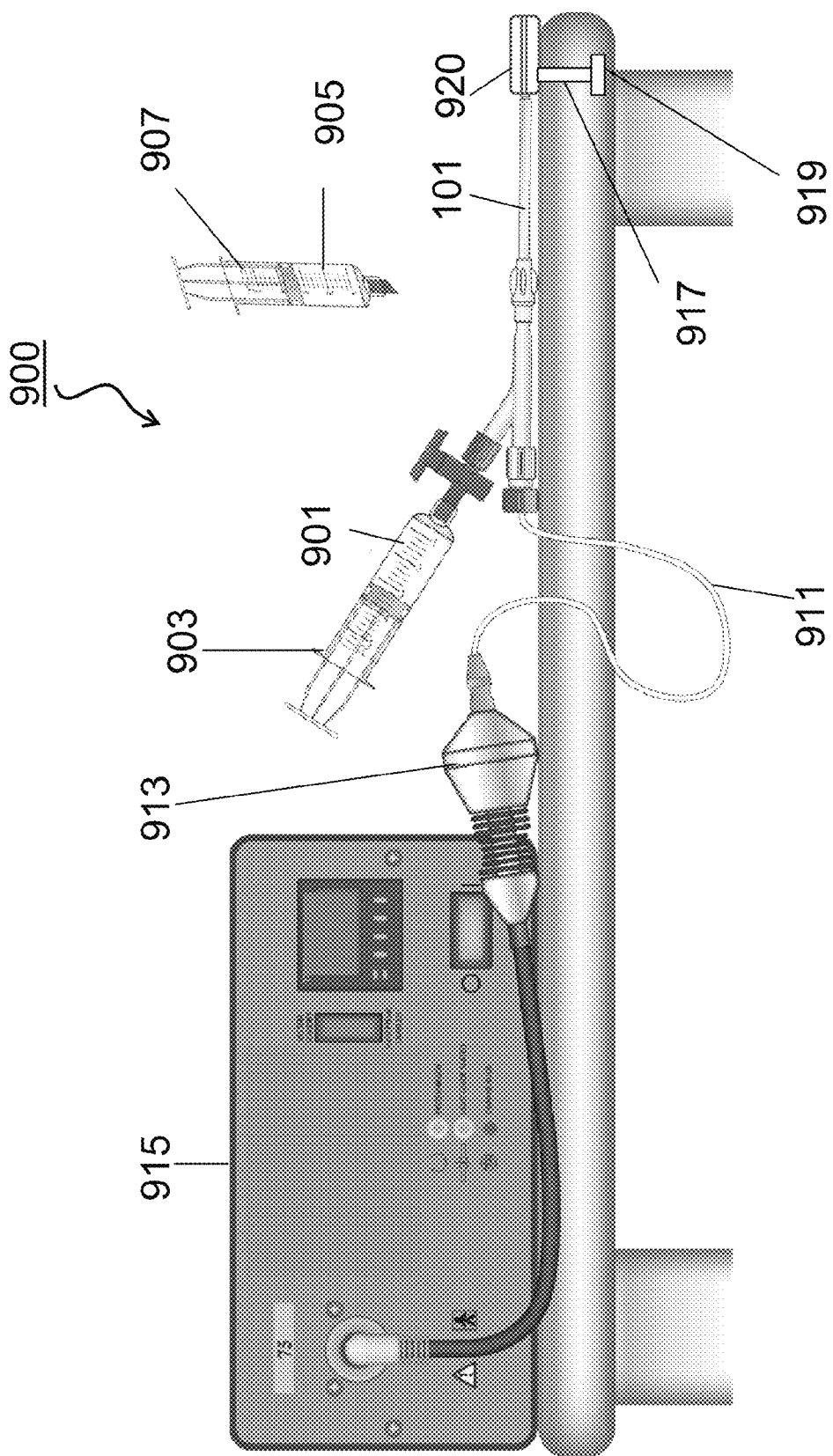
FIG. 9 is a schematic illustration of an embodiment of a kit for photodynamic bone stabilization and drug delivery of the present disclosure.

FIG. 9 is a schematic illustration of an embodiment of a kit 900 for photodynamic bone stabilization and drug delivery system of the present disclosure. The kit 900 includes a unit dose of a light sensitive liquid 901; an embodiment of an expandable portion 920, such as the expandable portion 200, 300, 400, 500, 600, or 700, releasably mounted on an insertion catheter 101, wherein the insertion catheter 101 has an inner void for passing the light-sensitive liquid 901 to the expandable portion, and one or more inner lumens, such as for passing a light-sensitive liquid 901 or an additive 905. In an embodiment, the light-sensitive liquid 901 is housed in syringe 903. In an embodiment, the syringe 903 maintains a low pressure during the infusion and aspiration of the light-sensitive liquid 901. In an embodiment, the kit 900 further includes a unit dose of at least one additive 905, which can be provided in a syringe 907. In an embodiment, the expandable portion 920 is in fluid communication with a flexible tube 917. The syringe 907 may be attached to a port 919 at a proximal end of the flexible tube 917 to fill the expandable portion with the additive 905 before or after the implantation of the expandable portion 920. In an embodiment, additional one or more additives may be added to the expandable section 920 throughout the healing process.

In an embodiment, the kit 900 further includes an optical fiber 911, wherein the optical fiber 911 is sized to pass through the inner lumen of the insertion catheter 101 to guide a light into the expandable portion to illuminate and cure the light-sensitive liquid 901. In an embodiment, an attachment system 913 communicates light energy from a light source 915 to the optical fiber 911. In an embodiment, the light source 915 emits frequency that corresponds to a band in the vicinity of 390 nm to 770 nm, the visible spectrum. In an embodiment, the light source 915 emits frequency that corresponds to a band in the vicinity of 410 nm to 500 nm. In an embodiment, the light source 910 emits frequency that corresponds to a band in the vicinity of 430 nm to 450 nm. In an embodiment, the light-sensitive liquid 901 is a liquid monomer hardenable by visible light energy emitted by the light source 915.

In an embodiment, a photodynamic bone stabilization system of the present disclosure includes an insertion catheter having an elongated shaft with a proximal end, a distal end, and a longitudinal axis therebetween, the insertion catheter having an inner void for passing at least one light-sensitive liquid, and an inner lumen; an expandable portion releasably engaging the distal end of the insertion catheter, wherein the expandable portion comprises: an inner expandable portion fabricated from a non-permeable material, wherein the inner expandable portion is in communication with the inner lumen of the insertion catheter and wherein the inner expandable portion is sufficiently designed to maintain a light-sensitive liquid within the inner expandable portion; and an outer expandable portion, surrounding the inner expandable portion, sufficiently designed to house and release at least one additive from the outer expandable portion in an outward direction from the inner expandable portion; and a light-conducting fiber, wherein the light-conducting fiber is sized to pass through the inner lumen of the insertion catheter and into the inner expandable portion for delivering light energy to the light-sensitive liquid.

In an embodiment, a photodynamic bone stabilization system of the present disclosure includes an insertion catheter having an elongated shaft with a proximal end, a distal end, and a longitudinal axis therebetween, the insertion catheter having an inner void for passing at least one light-sensitive liquid, and an inner lumen; an expandable portion releasably engaging the distal end of the insertion catheter, wherein the expandable portion is movable from a deflated state to an inflated state when a light-sensitive liquid is delivered to the expandable portion; one ore more surface layers disposed along an outer surface of the expandable portion, wherein the one or more surface layers are sufficiently designed to release at least one additive; and a light-conducting fiber, wherein the light-conducting fiber is sized to pass through the inner lumen of the insertion catheter and into the expandable portion for delivering light energy to the light-sensitive liquid.

In an embodiment, a method for repairing a fractured bone of the present disclosure includes the steps of delivering to an inner cavity of the fractured bone an expandable portion releasably engaging a distal end of an insertion catheter, wherein the expandable portion comprises: an inner expandable portion fabricated from a non-permeable material, wherein the inner expandable portion is in communication with an inner lumen of the insertion catheter and wherein the inner expandable portion is sufficiently designed to maintain a light-sensitive liquid within the inner expandable portion; and an outer expandable portion, surrounding the inner expandable portion, sufficiently designed to house and release at least one additive from the outer expandable portion in an outward direction from the inner expandable portion; and infusing a light-sensitive liquid through an inner void of the insertion catheter into the inner expandable portion to move the expandable portion from an initial deflated state to a final inflated state; inserting a light-conducting fiber into the inner lumen of the insertion catheter; activating the light-conducting fiber so as to cure the light sensitive liquid within the inner expandable portion; delivering at least one additive locally to the fractured bone by releasing the at least one additive from the outer expandable portion; and releasing the expandable portion from the insertion catheter.

All patents, patent applications, and published references cited herein are hereby incorporated by reference in their entirety. While the methods of the present disclosure have been described in connection with the specific embodiments thereof, it will be understood that it is capable of further modification. Furthermore, this application is intended to cover any variations, uses, or adaptations of the methods of the present disclosure, including such departures from the present disclosure as come within known or customary practice in the art to which the methods of the present disclosure pertain, and as fall within the scope of the appended claims.

What is claimed is:

1. A photodynamic bone stabilization and drug delivery system for repairing a fractured bone comprising:
    an insertion catheter having an elongated shaft with a proximal end, a distal end, and a longitudinal axis therebetween, the insertion catheter having an inner void for passing at least one light-sensitive liquid, and an inner lumen;
    an expandable portion releasably engaging the distal end of the insertion catheter, wherein the expandable portion comprises:
        an inner expandable portion fabricated from a non-permeable material, wherein the inner expandable portion is in communication with the inner lumen of the insertion catheter and wherein the inner expandable portion is sufficiently designed to maintain a light-sensitive liquid within the inner expandable portion; and
        an outer expandable portion, surrounding the inner expandable portion, sufficiently designed to house and release at least one additive from the outer expandable portion in an outward direction from the inner expandable portion and into an intramedullary canal of the fractured bone; and
    a light-conducting fiber, wherein the light-conducting fiber is sized to pass through the inner lumen of the insertion catheter and into the inner expandable portion for delivering light energy to the light-sensitive liquid to cure the light-sensitive liquid within the inner expandable portion,
    wherein at least one of an outer surface of the inner expandable portion or an inner surface of the outer expandable portion includes a textured surface.

2. The system of claim 1, wherein the light-conducting fiber emits light radially in a uniform manner along a length of the light-conducting fiber.

3. The system of claim 1, wherein the outer expandable portion includes one or more porous sections designed to release the at least one additive.

4. The system of claim 3, wherein the one or more porous sections of the outer expandable portion are fabricated from a non-porous polymer material.

5. The system of claim 3, wherein the one or more porous sections of the outer expandable portion are fabricated from a porous polymer material.

6. The system of claim 3, wherein the one or more porous sections of the outer expandable portion extend along a section of the outer expandable portion.

7. The system of claim 3, wherein the one or more porous sections include a plurality of pores having sizes and shapes that are substantially non-uniform throughout the porous section.

8. The system of claim 3, wherein the one or more porous sections include a plurality of pores having sizes and shapes that are substantially uniform throughout the porous section.

9. The system of claim 1, wherein the outer expandable portion is fabricated from a porous polymer.

10. The system of claim 1 further comprising a tube in fluid communication with the outer expandable portion and a port disposed at a distal end of the tube.

11. The system of claim 1, wherein the outer expandable portion and the inner expandable portion are fabricated from a thin-walled noncompliant material.

12. The system of claim 1, further comprising an adapter engaging the proximal end of the insertion catheter.

13. The system of claim 1, further comprising a syringe housing a light-sensitive liquid, the syringe engaging the proximal end of the insertion catheter.

14. The system of claim 1, further comprising a syringe housing at least one additive, the syringe attached to the proximal end of the insertion catheter.

15. The system of claim 1, wherein the light-conducting fiber is modified to alter a direction of a light.

16. The system of claim 1, wherein at least one of the insertion catheter, outer expandable portion or the inner expandable portion includes one or more radiopaque markers.

17. The system of claim 1, wherein the textured surface includes at least one of bumps, riblets, ribs, and ridges.

18. A photodynamic bone stabilization and drug delivery system for repairing a fractured bone comprising:
   an insertion catheter having an elongated shaft with a proximal end, a distal end, and a longitudinal axis therebetween, the insertion catheter having an inner void for passing at least one light-sensitive liquid, and an inner lumen;
   an expandable portion releasably engaging the distal end of the insertion catheter, wherein the expandable portion comprises:
      an inner expandable portion in communication with the inner lumen of the insertion catheter and sufficiently designed to maintain a light-sensitive liquid within the inner expandable portion; and
      an outer expandable portion, surrounding the inner expandable portion, sufficiently designed to house and release at least one additive from the outer expandable portion in an outward direction from the inner expandable portion, wherein the outer expandable portion includes one or more porous sections designed to release the at least one additive into an intramedullary canal of the fractured bone; and
   a light-conducting fiber, wherein the light-conducting fiber is sized to pass through the inner lumen of the insertion catheter and into the inner expandable portion for delivering light energy to the light-sensitive liquid to cure the light-sensitive liquid within the inner expandable portion,
   wherein at least one of an outer surface of the inner expandable portion or an inner surface of the outer expandable portion includes a textured surface.

19. The system of claim 18, wherein the one or more porous sections are designed to release the at least one additive from the outer expandable portion at a pre-determined flow.

20. A photodynamic bone stabilization and drug delivery system for repairing a fractured bone comprising:
   an insertion catheter having an elongated shaft with a proximal end, a distal end, and a longitudinal axis therebetween, the insertion catheter having an inner void for passing at least one light-sensitive liquid, and an inner lumen;
   an expandable portion releasably engaging the distal end of the insertion catheter, wherein the expandable portion comprises:
      a thin-walled non-compliant inner expandable portion in communication with the inner lumen of the insertion catheter sufficiently designed to stabilize the fractured bone, wherein the inner expandable portion is sufficiently designed to maintain a light-sensitive liquid within the inner expandable portion; and
      a thin-walled non-compliant outer expandable portion, surrounding the inner expandable portion, sufficiently designed to release at least one additive housed between the inner expandable portion and the outer expandable portion into an intramedullary canal of the fractured bone; and
   a light-conducting fiber, wherein the light-conducting fiber is sized to pass through the inner lumen of the insertion catheter and into the inner expandable portion for delivering light energy to the light-sensitive liquid to cure the light-sensitive liquid within the inner expandable portion,
   wherein at least one of an outer surface of the inner expandable portion or an inner surface of the outer expandable portion includes a textured surface.

* * * * *